United States Patent
Bakshi et al.

(10) Patent No.: US 11,669,793 B2
(45) Date of Patent: Jun. 6, 2023

(54) INTER-APPLICATION WORKFLOW PERFORMANCE ANALYTICS

(71) Applicant: Box, Inc., Redwood City, CA (US)

(72) Inventors: Rohit Bakshi, Campbell, CA (US); Daniel Wayne Morkovine, San Carlos, CA (US); Faizan N. Buzdar, Redwood City, CA (US)

(73) Assignee: Box, Inc., Redwood City, CA (US)

( * ) Notice: Subject to any disclaimer, the term of this patent is extended or adjusted under 35 U.S.C. 154(b) by 22 days.

(21) Appl. No.: 16/726,081

(22) Filed: Dec. 23, 2019

(65) Prior Publication Data

US 2020/0134518 A1    Apr. 30, 2020

Related U.S. Application Data

(60) Provisional application No. 62/909,116, filed on Oct. 1, 2019.

(51) Int. Cl.
*G06Q 10/0633* (2023.01)
*G06Q 30/0201* (2023.01)
(Continued)

(52) U.S. Cl.
CPC ..... *G06Q 10/0633* (2013.01); *G06Q 10/0637* (2013.01); *G06Q 10/06393* (2013.01); *G06Q 30/0201* (2013.01)

(58) Field of Classification Search
None
See application file for complete search history.

(56) References Cited

U.S. PATENT DOCUMENTS 9,148,425 B2    9/2015 Rowe et al.
10,038,731 B2    7/2018 Pearl et al.
(Continued)

FOREIGN PATENT DOCUMENTS

CN    108256788 A    *    7/2018

OTHER PUBLICATIONS

English Translation of CN-108256788-A, translated on Sep. 28, 2021 (original reference published on Jul. 6, 2018).*

(Continued)

*Primary Examiner* — Susanna M. Diaz
(74) *Attorney, Agent, or Firm* — Vista IP Law Group, LLP

(57) ABSTRACT

Methods, systems and computer program products for shared content management systems that provide performance analytics pertaining to a project. Embodiments include establishing one or more network communication links between a content management system that manages a plurality of shared content objects and a plurality of applications that cause modifications to the shared content objects in accordance with workflows of the project. Iteraction events that correspond to modifications over the shared content objects are recorded such that interaction events associated with the plurality of applications are selected based at least in part on attributes associated with the interaction events. Relationships between the recorded interaction events such as time durations between certain of the interaction events are calculated. Project performance measurements are generated based on the calculations and/or based on other relationships between the interaction events. The calculations may span across many different applications and/or many different departments and/or many different enterprises.

20 Claims, 11 Drawing Sheets

(51) Int. Cl.
G06Q 10/0637 (2023.01)
G06Q 10/0639 (2023.01)

(56) References Cited

U.S. PATENT DOCUMENTS

| | | | |
|---|---|---|---|
| 10,176,435 B1* | 1/2019 | Sarkar | G06N 20/00 |
| 10,331,416 B2 | 6/2019 | Chaudhry et al. | |
| 10,540,624 B2 | 1/2020 | Hui et al. | |
| 10,922,282 B2 | 2/2021 | Jalagam et al. | |
| 2004/0049481 A1 | 3/2004 | Blevins | |
| 2004/0260593 A1* | 12/2004 | Abraham-Fuchs | G06Q 10/06398 705/7.26 |
| 2006/0074703 A1 | 4/2006 | Bhandarkar et al. | |
| 2007/0005388 A1* | 1/2007 | Busch | G06Q 10/063 705/342 |
| 2007/0157210 A1* | 7/2007 | Inoue | H04L 41/5096 718/105 |
| 2007/0203589 A1 | 8/2007 | Flinn et al. | |
| 2007/0265900 A1 | 11/2007 | Moore et al. | |
| 2008/0114791 A1 | 5/2008 | Takatsu et al. | |
| 2008/0183536 A1* | 7/2008 | Hirabayashi | G06Q 10/06 382/100 |
| 2009/0172101 A1* | 7/2009 | Arthursson | G06F 9/452 709/205 |
| 2009/0249290 A1 | 10/2009 | Jenkins et al. | |
| 2011/0004583 A1* | 1/2011 | Honda | G06F 16/24539 707/609 |
| 2012/0239739 A1* | 9/2012 | Manglik | G06F 8/61 709/203 |
| 2012/0290346 A1 | 11/2012 | Breiter et al. | |
| 2013/0275475 A1 | 10/2013 | Ahlborn | |
| 2015/0067028 A1 | 3/2015 | Kumar et al. | |
| 2015/0082271 A1 | 3/2015 | Damonte et al. | |
| 2015/0088924 A1 | 3/2015 | Abadi et al. | |
| 2015/0149535 A1 | 5/2015 | Howard | |
| 2017/0048285 A1 | 2/2017 | Pearl et al. | |
| 2017/0068915 A1 | 3/2017 | Nair | |
| 2017/0168765 A1 | 6/2017 | Fan et al. | |
| 2017/0264567 A1 | 9/2017 | Shetty et al. | |
| 2017/0316363 A1 | 11/2017 | Siciliano et al. | |
| 2019/0026663 A1 | 1/2019 | Homeyer et al. | |
| 2019/0332695 A1 | 10/2019 | Bensberg et al. | |
| 2020/0050330 A1 | 2/2020 | Schilling et al. | |
| 2020/0065152 A1 | 2/2020 | Parmar et al. | |
| 2020/0065313 A1 | 2/2020 | Patel et al. | |
| 2020/0301674 A1 | 9/2020 | Swope et al. | |
| 2020/0380432 A1* | 12/2020 | Wang | G06Q 10/0633 |
| 2020/0389543 A1 | 12/2020 | Swope et al. | |
| 2021/0004273 A1 | 1/2021 | You et al. | |
| 2022/0083679 A1 | 3/2022 | Hiller et al. | |

OTHER PUBLICATIONS

Final Office Action for U.S. Appl. No. 16/948,829 dated Mar. 1, 2022.
Non-Final Office Action dated Apr. 20, 2021 for related U.S. Appl. No. 16/553,144.
Bellini, et al. A Workflow Model and Architecture for Content and Metadata Management Based on Grid Computing. ECLAP 2013, pp. 118-127. (Year: 2013).
Belhajjame et al. Metadata Management in the Taverna Workflow System. IEEE International Symposium on Cluster Computing and the Grid, 2008, pp. 651-656. (Year: 2008).
Final Office Action dated Aug. 31, 2021 for related U.S. Appl. No. 16/553,144.
Glatard, T. et al., "Software architectures to integrate workflow engines in science gateways", Future Generation Computer Systems, vol. 75, (Oct. 2017).
Duranova, E. "Data Object Classes", DNAnexus, (last edited on Oct. 4, 2018).
"Informatica® Test Data Management 10.2.1", User Guide, (May 2018).
Zalcman, A. "Developer Tutorials/Workflow Build Process", DNAnexus, (last edited on Oct. 4, 2018).
Salesforce, "Metadata API Developer Guide", Version 46.0, Summer'19, (Last updated: May 22, 2019).
IBM Cúram Social Program Management, Cúram Workflow Reference Guide, Version 6.0.4.
Non-Final Office Action dated Nov. 8, 2021 for realated U.S. Appl. No. 16/553,161.
Vardigan, Mary, et al. "Creating Rich, Structured Metadata: Lessons Learned in the Metadata Portal Project." IASSIST Quarterly 38.3 (2015): 15-15.
Jensen et al. Using Characteristics of Computational Science Schemas for Workflow Metadata Management. IEEE Congress on Services 2008—Part I, pp. 445-452. (Year: 2008).
Non-Final Office Action for U.S. Appl. No. 16/553,144 dated Mar. 10, 2022.
Notice of Allowance for U.S. Appl. No. 16/726,093 dated Feb. 25, 2022.
Final Office Action for U.S. Appl. No. 16/553,161 dated Mar. 21, 2022.
Final Office Action for U.S. Appl. No. 16/726,093 dated Oct. 26, 2021.
Non-Final Office Action for U.S. Appl. No. 16/726,093 dated Apr. 15, 2021.
Non-Final Office Action for U.S. Appl. No. 16/948,829 dated Sep. 15, 2021.
Geisriegler, "Actor Based Business Process Modeling and Execution: a Reference Implementation Based on Ontology Models and Microservices," 2017 43rd Euromicro Conference on Software Engineering and Advanced Applications (S EAA) , pp. 359-362 (Year: 2017).
Koschmider, "Recommendation-based editor for business process modeling," 2011, Data & Knowledge Engineering, vol. 70, pp. 483-503 (Year: 2011).
"SharePoint 2013 Workflow—Dynamic Values", AndrewConnell, dated Jul. 17, 2012, URL: https://www.andrewconnell.com/blog/SP2013-Workflow-Dynamic-Values/.
"Workflow Variable Datatype Conversion", Informatica, dated Apr. 15, 2019, URL: https://docs.informatica.com/data-integration/data-services/10-2/developer-workflow-guide/workflow-variables/workflow-variable-datatype-conversion.html.
"Creating Dynamic Variable Types", UIPath Forum, dated Aug. 2019, URL: https://forum.uipath.com/t/creating-dynamic-variable-types/141077.
"Developing Web Views for VMware vCenter Orchestrator", vRealize Orchestrator 5.5, vmware, copyright 2017.
"VMware vCenter Orchestrator 5.5 Release Notes", Vmware, dated Jun. 26, 2017.
"Developing with Vmware vCenter Orchestrator," vRealize Orchestrator 5.5.1, copyright 2014.
"Developing a Web Services Client for VMware vCenter Orchestrator," vRealize Orchestrator 5.5.1, copyright 2014.
"VMware vCenter Orchestrator 5.5.1 Release Notes", vmware, dated Jun. 23, 2017.
"Using the Vmware vCenter Orchestrator Client," vRealize Orchestrator 5.5.1, Copyright 2014.
"Installing and Configuring Vmware vCenter Orchestrator," vRealize Orchestrator 5.5.2, Copyright 2014.
"VMware vCenter Orchestrator 5.5.2 Release Notes," vmware, dated Jun. 16, 2017.
"Using VMware vCenter Orchestrator Plug-Ins," vRealize Orchestrator 5.5.2, Copyright 2014.
"VMware vCenter Orchestrator 5.5.3 Release Notes," vmware, dated Jun. 23, 2017.
"VMware vCenter Orchestrator 5.5.2.1 Release Notes," vmware, dated Jun. 16, 2017.
"ProcessMaker Advanced Workflow for DocuSign," DocuSign, date obtained via Google as 2018, URL: https://partners.docusign.com/s/partner-solution/aNR1W000000001I/processmaker-advanced-workflow-for-docusign-esignature.
"DocuSign Electronic Signature Workflow," ProcessMaker, date obtained via Google as Dec. 5, 2016, URL: https://www.processmaker.com/landing/processmaker-docusign/.

(56) References Cited

OTHER PUBLICATIONS

Glatard, T., et al. "Software architectures to integrate workflow engines in science gateways," Future Generation Computer Systems vol. 75, Oct. 2017, pp. 239-255.

"Data Object Classes," copyright 2013, DNAnexus, Inc.

"Metadata API Developer Guide," SalesForce, Version 46.0, dated 2019.

"Cúram Workflow Reference Guide," Version 6.0.4, Copyright 2011, Cúram Software Limited.

"Developer Tutorials/Workflow Build Process," copyright 2013, DNAnexus, Inc.

"IBM Case Manager target object store extensions," IBM Corporation, Copyright 2016.

Vardigan, M., et al., "Creating Rich, Structured Metadata: Lessons Learned in the Metadata Portal Project," IASSIST Quarterly, dated 2014.

"User Guide," Informatica® Test Data Management 10.2.1, dated May 2018.

"Do more with Dropbox using your favorite tools," Dropbox, date found via Internet Archive as Mar. 8, 2021, URL: https://www.dropbox.com/features/extensions.

"Build better campaigns with Dropbox for Salesforce Marketing Cloud," Dropbox Team, dated Jun. 17, 2019, URL: https://blog.dropbox.com/topics/product-tips/dropbox-marketing-cloud.

Notice of Allowance for U.S. Appl. No. 16/726,093 dated Apr. 14, 2022.

Notice of Allowance dated Sep. 21, 2022 for U.S. Appl. No. 17/447,562.

Final Office Action For U.S. Appln. No. 16/553,144 dated Aug. 5, 2022.

Notice of Allowance for U.S. Appl. No. 16/726,093 dated Aug. 31, 2022.

Non-Final Office Action for U.S. Appl. No. 16/553,161 dated Aug. 15, 2022.

Notice of Allowance dated Dec. 30, 2022 for U.S. Appl. No. 16/726,093.

Notice of Allowance dated Feb. 15, 2023 for U.S. Appl. No. 16/726,093.

Non-Final Office Action dated Feb. 17, 2023 for U.S. Appl. No. 16/553,144.

Non-Final Office Action dated Feb. 28, 2023 for U.S. Appl. No. 16/948,829.

Final Office Action for U.S. Appl. No. 16/553,161 dated Jan. 24, 2023.

* cited by examiner

INTER-APPLICATION WORKFLOW PERFORMANCE ANALYTICS

RELATED APPLICATIONS

The present application claims the benefit of priority to U.S. Patent Application Ser. No. 62/909,116 titled "INTER-APPLICATION WORKFLOW PERFORMANCE ANALYTICS", filed on Oct. 1, 2019, which is hereby incorporated by reference in its entirety.

FIELD

This disclosure relates to shared content management systems, and more particularly to techniques for generating and presenting inter-application workflow performance analytics.

BACKGROUND

High-performance computing, storage, and networking capabilities characteristic of today's computing environments have impacted the way personal and corporate computer-readable content objects (e.g., documents, spreadsheets, images, programming code files, etc.) are created, stored, and shared. The capabilities of these environments facilitate interactions (e.g., authoring, editing, viewing, etc.) that are performed over content objects by trusted users (e.g., collaborators) on a variety of user devices such as mobile phones, tablets, laptop computers, desktop computers, and/or other devices. In many cases, interactions over the content objects are organized into workflows. Such workflows often specify an ordered sequence or "flow" of operations to be performed on the content objects, which operations are often invoked by user interactions with the content objects. Interactions with a particular content object may be performed by one user, multiple users, and/or even autonomously by one or more computing entities (e.g., processes, agents, applications, etc.). Moreover, such interactions may span across multiple departments and/or multiple enterprises.

Modern computing environments facilitate the proliferation and use of numerous applications that are accessed by the users to carry out the foregoing interactions over content objects. These applications (e.g., application-specific tools, point tools, etc.) are often used to improve the efficiency of the interactions performed over the content objects. A particular application may be selected from the hundreds of applications available in a computing environment for a variety of reasons such as: (1) familiarity and/or proficiency of users with the application, (2) popularity and/or functionality of the application as pertains to a particular content object type and/or a particular interaction (e.g., operation) over that content object type, and/or (3) for other reasons.

As merely one example, several members of the sales department might use a customer relationship management (CRM) tool and a real-time messaging tool to perform various interactions and/or workflows over certain content objects (e.g., a proposal slide deck, an ROI analysis worksheet, etc.) that are associated with a particular sales opportunity. At some point in the sales engagement, a draft contract might be created and sent to outside counsel for their review and possible modification, which interactions might involve the use of a document editing tool, possibly in conjunction with a document revisions tracking tool. When the contract is finalized and signed by the customer, a successful contract execution event will spawn new interactions and/or workflows over new content objects (e.g., onboarding forms, training materials, etc.). Over the project lifecycle of the foregoing sales deal, many users over multiple departments and enterprises may interact with many content objects using numerous applications to carry out the workflows and achieve the objectives of the deal.

Unfortunately, there is no mechanism for measuring the performance of workflows that involve interactions over content objects that are performed at multiple applications. Consider, for example, the aforementioned sales deal scenario. In this scenario, one or more of the users (e.g., a sales director) may desire to know the time to complete certain workflows (e.g., complete proposal, draft contract, sign contract, etc.) that are performed over the project lifecycle of the sales deal. Another one of the users (e.g., a sales program manager) might desire to know how much time is spent using the applications (e.g., point tools) over the project lifecycle of the sales deal. One approach to measuring such performance metrics is to have the users manually log all of the inter-application interactions performed over the content objects. In highly collaborative environments that span multiple users and enterprises and use many applications, such an approach is a burden to the users that detracts from the collaborative efficiency of the users. What is needed is a way to automatically monitor inter-application interactions with content objects so as to be able to measure various key metrics over the lifecycle of the interactions.

SUMMARY

The present disclosure describes techniques used in systems, methods, and in computer program products for inter-application workflow performance analytics, which techniques advance the relevant technologies to address technological issues with legacy approaches. More specifically, the present disclosure describes techniques used in systems, methods, and in computer program products for measuring the performance of workflows performed over multiple applications that are hosted on multiple heterogeneous computing systems. Certain embodiments are directed to technological solutions for linking content object interactions that are performed across multiple applications so as to generate sales engagement performance measurements of workflows that comprise the interactions.

The disclosed embodiments modify and improve over legacy approaches. In particular, the herein-disclosed techniques provide technical solutions that address the technical problems attendant to measuring the performance of workflows performed over multiple applications. Such technical solutions involve specific implementations (i.e., data organization, data communication paths, module-to-module interrelationships, etc.) that relate to the software arts for improving computer functionality.

The ordered combination of steps of the embodiments serve in the context of practical applications that perform steps for linking content object interactions that are performed across multiple applications so as to generate workflow performance measurements. As such, these techniques for linking content object interactions that are performed across multiple applications overcome long standing yet heretofore unsolved technological problems associated with measuring the performance of workflows performed over multiple applications.

Many of the herein-disclosed embodiments for linking content object interactions that are performed across multiple applications so as to generate performance measurements of workflows that comprise the interactions are technological solutions pertaining to technological problems that arise in the hardware and software arts that underlie deployment and use of workflows in content management systems. Aspects of the present disclosure achieve performance and other improvements in peripheral technical fields including (but not limited to) human-machine interfaces and distributed storage systems.

Further details of aspects, objectives, and advantages of the technological embodiments are described herein, and in the drawings and claims.

BRIEF DESCRIPTION OF THE DRAWINGS

The drawings described below are for illustration purposes only. The drawings are not intended to limit the scope of the present disclosure.

DETAILED DESCRIPTION

Figure 1:
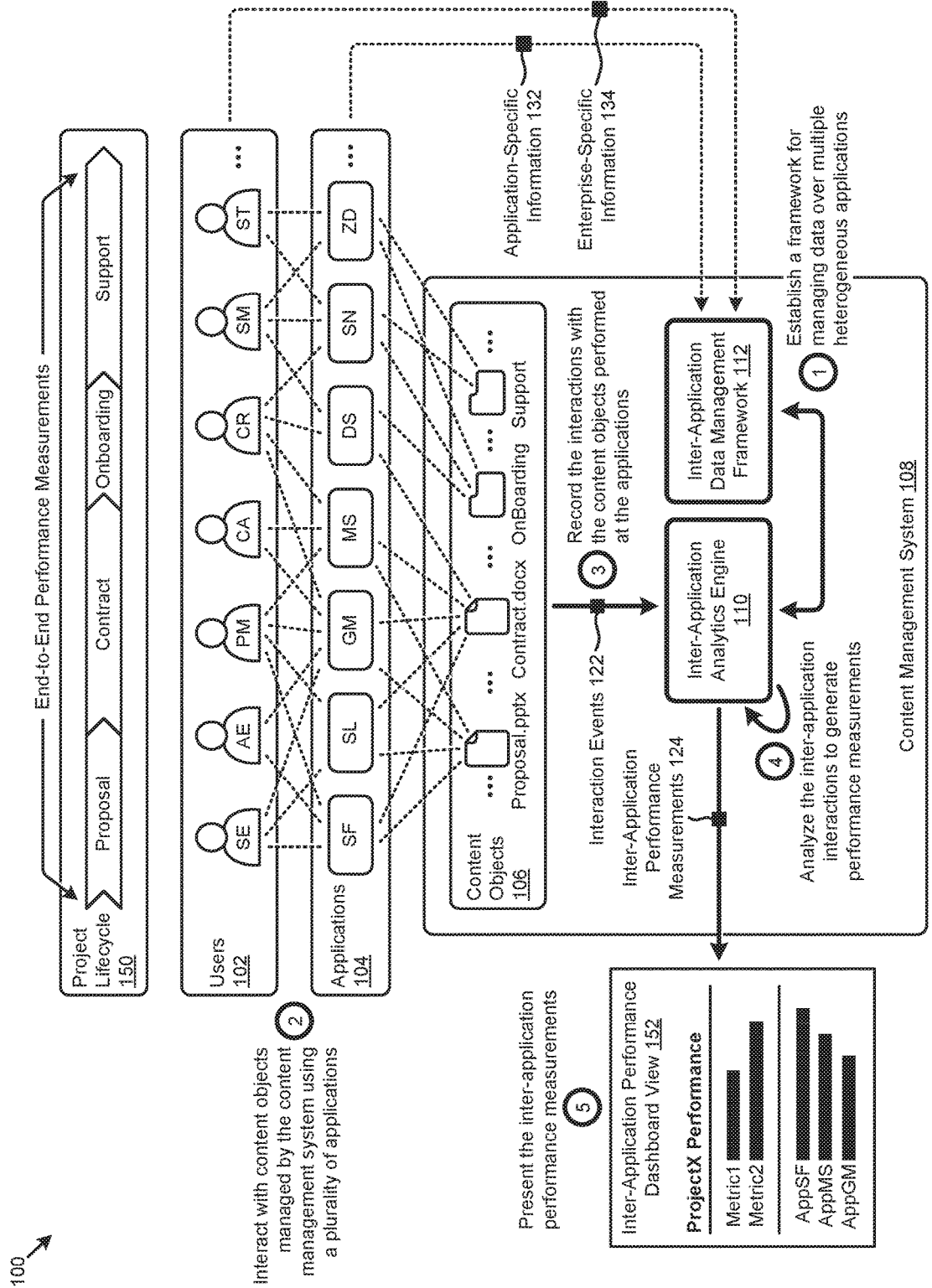
FIG. 1 illustrates a computing environment in which embodiments of the present disclosure can be implemented.

Aspects of the present disclosure solve problems associated with using computer systems for measuring the performance of workflows performed over multiple applications. These problems are unique to, and may have been created by, various computer-implemented methods for measuring the performance of workflows performed over multiple applications in the context of content management systems. Some embodiments are directed to approaches for linking content object interactions that are performed across multiple applications so as to generate performance measurements of workflows that comprise the interactions. The accompanying figures and discussions herein present example environments, systems, methods, and computer program products for measuring the performance of workflows performed over multiple applications.

Overview

Disclosed herein are techniques for linking interactions associated with content objects performed over multiple applications to generate performance measurements of workflows that comprise the linked interactions. In certain embodiments, the techniques are implemented in a computing environment comprising a content management system that facilitates interactions over a plurality of content objects that are created by, or modified by, or accessed by a plurality of applications. The applications available in the computing environment can include a native application (e.g., browser portal, mobile application, etc.) that is provided by the content management system and is accessed by its users (e.g., managed users) to facilitate certain interactions (e.g., authoring, editing, viewing, etc.) with and/or modifications to the content objects. Such modification to the content objects are modifications that arise from operations performed by an application during the lifecycle of a project. For example, at several moments during the prosecution of a sales engagement, a contract might be signed many times using a document signing application. As another example, at some point during the course of a sales engagement (e.g., after signing the contract), an onboarding form might be populated from a signed contract using a data import application.

The applications may comprise third-party applications that are available in the overall computing environment. Such third-party applications are applications that are not provided and/or maintained by the provider of the content management system, but rather are applications that are integrated with the content management system to facilitate certain interactions with at least some of the types of content objects managed at the content management system.

When users interact with content objects using the applications, the corresponding interaction events are recorded at the content management system. Certain specialized data structures are implemented in the content management system to facilitate recording of interaction events that arise at multiple heterogeneous applications. At certain moments in time, the interaction events associated with the applications are processed to select specific subsets of interaction events. For example, a request might be issued from a native application (e.g., at direction of a user) so as to select a set of interaction events that correspond to a particular project (e.g., sales engagement) lifecycle. Performance measurements associated with various workflow performance metrics are generated from the selected interaction events. As an example, the workflow performance metrics might pertain to various aspects of a sales engagement lifecycle. Visual representations of the performance measurements are then formed and presented to one or more of the users. In certain embodiments, a dashboard of workflow performance metrics might be populated with the performance measurements and presented to a user at a user interface. In certain embodiments, workflow performance metrics for a particular project lifecycle might pertain to the entire project lifecycle, or might pertain to particular workflows of the project, or might pertain to particular operations of the workflows, and/or other aspects of the project lifecycle.

Definitions and Use of Figures

Some of the terms used in this description are defined below for easy reference. The presented terms and their respective definitions are not rigidly restricted to these definitions—a term may be further defined by the term's use within this disclosure. The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application and the appended claims, the term "or" is intended to mean an inclusive "or" rather than an exclusive "or". That is, unless specified otherwise, or is clear from the context, "X employs A or B" is intended to mean any of the natural inclusive permutations. That is, if X employs A, X employs B, or X employs both A and B, then "X employs A or B" is satisfied under any of the foregoing instances. As used herein, at least one of A or B means at least one of A, or at least one of B, or at least one of both A and B. In other words, this phrase is disjunctive. The articles "a" and "an" as used in this application and the appended claims should generally be construed to mean "one or more" unless specified otherwise or is clear from the context to be directed to a singular form.

Various embodiments are described herein with reference to the figures. It should be noted that the figures are not necessarily drawn to scale, and that elements of similar structures or functions are sometimes represented by like reference characters throughout the figures. It should also be noted that the figures are only intended to facilitate the description of the disclosed embodiments—they are not representative of an exhaustive treatment of all possible embodiments, and they are not intended to impute any limitation as to the scope of the claims. In addition, an illustrated embodiment need not portray all aspects or advantages of usage in any particular environment.

An aspect or an advantage described in conjunction with a particular embodiment is not necessarily limited to that embodiment and can be practiced in any other embodiments even if not so illustrated. References throughout this specification to "some embodiments" or "other embodiments" refer to a particular feature, structure, material or characteristic described in connection with the embodiments as being included in at least one embodiment. Thus, the appearance of the phrases "in some embodiments" or "in other embodiments" in various places throughout this specification are not necessarily referring to the same embodiment or embodiments. The disclosed embodiments are not intended to be limiting of the claims.

Descriptions of Example Embodiments

FIG. 1 illustrates a computing environment 100 in which embodiments of the present disclosure can be implemented. As an option, one or more variations of computing environment 100 or any aspect thereof may be implemented in the context of the architecture and functionality of the embodiments described herein.

FIG. 1 illustrates aspects pertaining to linking content object interactions that are performed across multiple applications so as to generate performance measurements of workflows that comprise the interactions. Specifically, the figure presents a logical depiction of how certain of the herein disclosed techniques can be used to generate inter-application performance measurements from interactions performed over multiple applications. A representative scenario and set of high order operations are also presented to illustrate how the herein disclosed techniques are applied in computing environment 100.

The logical depiction of FIG. 1 depicts a representative set of users 102 who interact with various instances of content objects 106 managed at a content management system 108. Users 102 may be users (e.g., managed users) of content management system 108 that facilitates interactions (e.g., authoring, editing, viewing, etc.) over content objects 106 for sharing, collaboration, and/or other purposes. In some cases, such interactions are organized into workflows. Interactions and/or workflows over a particular content object may be performed with some human interaction by one or more of users 102 and/or with autonomous interaction by one or more computing entities (e.g., processes, agents, applications, etc.).

As can be observed, users 102 interact with content objects 106 and/or other users by accessing a plurality of applications 104. As merely one example, applications 104 might comprise instances of a native application provided by content management system 108 to facilitate the interactions of users 102 with content objects 106 and/or interactions with one another. As an example, the native application might be a browser portal or mobile application accessed by a user to manage a set of content objects that the user has authority to access. Applications 104 might also comprise various third-party applications. A third-party application might be a web application, mobile application, or another type of application that is served by a third-party server and accessed by some or all of users 102 to perform the aforementioned interactions. In this case, the applications are referred to as "third-party applications" as they are provided (e.g., developed, delivered, served, maintained, etc.) by an entity (e.g., the owner of the third-party server) other than the entity providing the content management system 108.

While such third-party applications are applications that are not provided and/or maintained by content management system 108, applications 104 may still be integrated with content management system 108 to facilitate certain interactions with at least some of the types of content objects 106 managed at content management system 108. Such integration may include registration of applications 104 with content management system 108, establishment of APIs to facilitate communication between the applications and system, and/or other integration capabilities.

In many cases, applications 104 can improve the efficiency of the interactions performed over content objects 106. A particular application may be selected from the hundreds of applications available in computing environment 100 for a variety of reasons, such as the familiarity and/or proficiency of users with the application, the popularity and/or functionality of the application as pertains to a particular content object type, and/or a particular interaction (e.g., operation) over that content object type, and/or for other reasons. As such, workflows over a particular content object might be performed entirely at one or more of the applications 104, entirely at content management system 108, or at some combination of one or more of applications 104 and content management system 108.

Referring to the example scenario illustrated in FIG. 1, consider that certain users access various applications to interact with a set of content objects so as to carry out constituent stages of a project lifecycle 150. Specifically, project lifecycle 150 might pertain to a project associated with a particular customer and comprise a "Proposal" stage, a "Contract" stage, an "Onboarding" stage, and a "Support" stage. To achieve the objectives of each stage and the overall project, many users over multiple departments and enterprises interact with many content objects using numerous applications to carry out the various workflows associated with the project. In the shown scenario, the users involved over project lifecycle 150 include a sales engineer (e.g., user "SE"), an applications engineer (e.g., user "AE"), a program manager (e.g., user "PM"), a contract attorney (e.g., user "CA"), a customer representative (e.g., user "CR"), a service manager (e.g., user "SM"), a service technician (e.g., user "ST"), and/or other users. As merely examples, the foregoing users might access a SalesForce application (e.g., app "SF"), a Slack application (e.g., app "SL"), a Gmail application (e.g., app "GM"), a Microsoft application (e.g., app "MS"), a DocuSign application (e.g., app "DS"), a ServiceNow application (e.g., app "SN"), a ZenDesk application (e.g., app "ZD"), and/or other applications to interact with various content objects (e.g., a "Proposal.pptx" file, a "Contract.docx" file, an "OnBoarding" folder and underlying files, a "Support" folder and underlying files, etc.) over project lifecycle 150.

In this scenario, one or more of the aforementioned users or another user (e.g., a sales director) may desire to know the time to complete certain workflows (e.g., complete proposal, draft and sign contract, etc.). Moreover, a different user (e.g., a sales VP) may want to analyze end-to-end performance measurements that pertain to the various actions that are carried out during the course of a sales engagement. A still different user or different type of user (e.g., user "PM") might desire to know how much time is spent using the applications (e.g., point tools) and how such usage relates to achievement of various specific objectives that are accomplished over the duration of the project. However, unfortunately, there are no mechanisms for measuring the performance of workflows that involve interactions over content objects 106 that are performed over heterogeneous instances of applications 104.

The herein disclosed techniques address such challenges pertaining to measuring the performance of workflows performed over multiple applications at least in part by linking interactions associated with content objects 106 performed over multiple heterogeneous instances of applications 104 to generate performance measurements of workflows that comprise the interactions.

In the embodiment of FIG. 1, the techniques are facilitated at least in part by an inter-application analytics engine 110 implemented at content management system 108. An inter-application data management framework 112 is also established at content management system 108 to facilitate management of any data pertaining to interactions performed over content objects at multiple heterogeneous applications (operation 1). More specifically, inter-application data management framework 112 comprises various specialized data structures that, at least in part, link the interactions performed over content objects at multiple heterogeneous applications. As used herein, an inter-application data management framework is any operational element that receives and stores information from a plurality of applications so as to facilitate subsequent querying and retrievals by another operational element.

As indicated in the figure, at least some of the data structures of inter-application data management framework 112 are used to organize and store application-specific information 132 associated with applications 104 (e.g., application attributes, workflow states, task states, etc.) and/or enterprise-specific information 134 (e.g., workflow definitions, interaction definitions, metric definitions, etc.) associated with users 102. When users 102 interact with content objects 106 using any of the applications 104 (operation 2), certain event attributes that correspond to respective instances of interaction events 122 are recorded by inter-application analytics engine 110 at content management system 108 (operation 3). Such event attributes may comprise attributes that describe the interaction and other attributes that describe certain entities (e.g., users, content objects, workflows, etc.) associated with the interaction events. According to the herein disclosed techniques, the event attributes might also comprise one or more link attributes that facilitate the aforementioned links between the applications.

The foregoing event attributes associated with inter-application interactions are analyzed by inter-application analytics engine 110 to generate one or more inter-application performance measurements 124 (operation 4). As can be observed, data organized and stored in accordance with inter-application data management framework 112 is often accessed by inter-application analytics engine 110 to generate one or more of the inter-application performance measurements 124. For example, certain enterprise-specific metric definitions organized according to the inter-application data management framework 112 might be queried by inter-application analytics engine 110 to retrieve a performance measurement for a particular metric.

The inter-application performance measurements determined by the herein disclosed techniques are then presented to one or more of users 102 (operation 5). As an example, the set of inter-application performance measurements 124 may be presented to a user at the user interface of a native application. In one example, as shown, an inter-application performance dashboard view 152 presented at the user interface graphically depicts performance measurements associated with "ProjectX", which performance measurements include a measurement associated with a first metric "Metric1", a measurement associated with a second metric "Metric2", as well as additional performance measurements associated with applications "SF", "MS", and "GM", which are shown as "AppSF", "AppMS", and "AppGM", respectively.

The automatic inter-application performance analytics capability facilitated by the herein disclosed techniques serves to address the problems attendant to measuring the performance of workflows performed over multiple applications. As such, application of the techniques disclosed herein facilitate improvements in computer functionality that serve to reduce the demand for computer memory, reduce the demand for computer processing power, reduce network bandwidth use, and reduce the demand for inter-component communication. Specifically, consumption of computing resources that might be needed to at least facilitate manual recording and aggregation of interactions performed over a large number of users, content objects, and applications is eliminated.

One embodiment of techniques for such automatic inter-application performance analytics is disclosed in further detail as follows.

Figure 2:
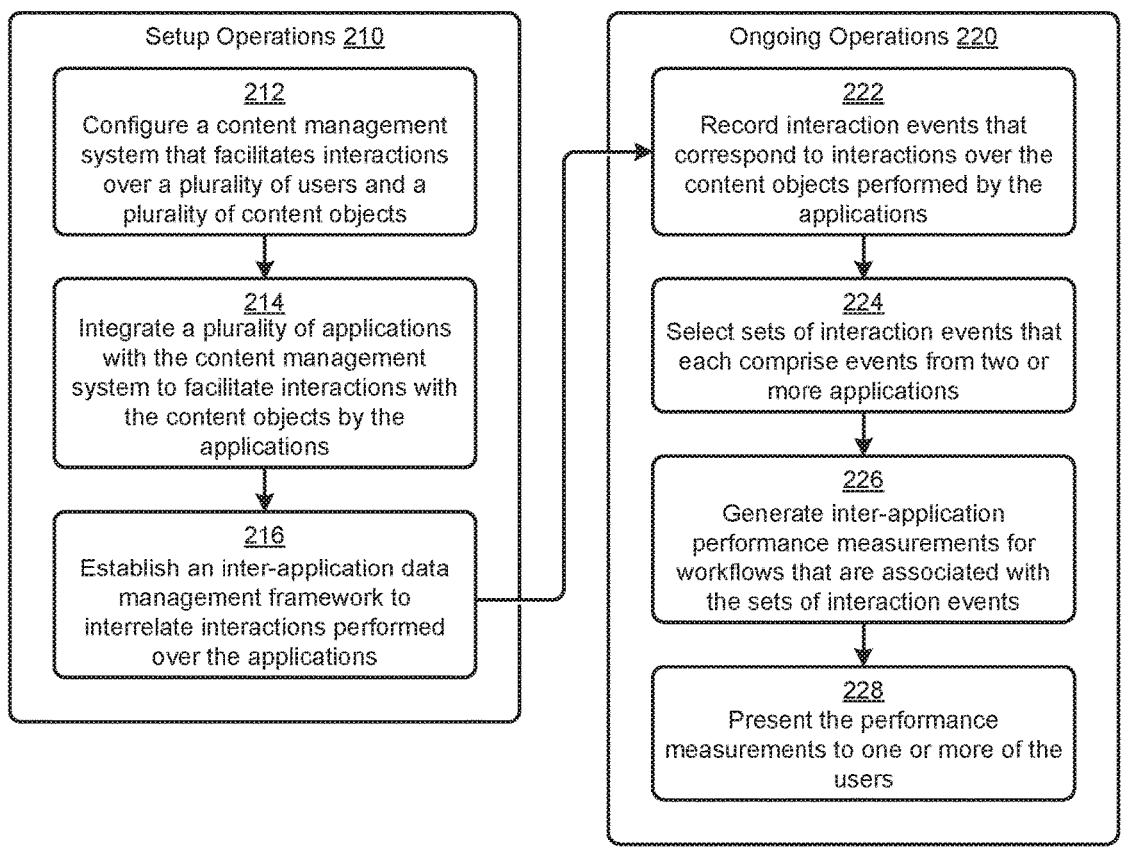
FIG. 2 is a flowchart depicting an inter-application workflow performance analysis technique as implemented in systems that measure the performance of workflows performed over multiple applications, according to an embodiment.

FIG. 2 is a flowchart depicting an inter-application workflow performance analysis technique 200 as implemented in systems that measure the performance of workflows performed over multiple applications. As an option, one or more variations of inter-application workflow performance analysis technique 200 or any aspect thereof may be implemented in the context of the architecture and functionality of the embodiments described herein. The inter-application workflow performance analysis technique 200 or any aspect thereof may be implemented in any environment.

FIG. 2 illustrates aspects pertaining to linking content object interactions that are performed across multiple applications so as to generate performance measurements of workflows that comprise the interactions. Specifically, the figure is presented to illustrate one embodiment of certain steps and/or operations performed over a network of devices (e.g., user devices, computing systems, etc.) to record and analyze interactions over content objects performed at multiple heterogeneous applications to generate inter-application performance measurements. As can be observed, the steps and/or operations can be grouped into a set of setup operations 210 and a set of ongoing operations 220.

Setup operations 210 of inter-application workflow performance analysis technique 200 commences by identifying or configuring a content management system that facilitates interactions over a plurality of users and a plurality of content objects (step 212). Such interactions can involve both user-to-user interactions and user-to-content interactions. A plurality of applications (e.g., apps) are integrated with the content management system to facilitate interactions over the users and/or content objects performed by the apps (step 214). As an example, a sales contract document managed by the content management system might be shared using a first application (e.g., SalesForce) to facilitate the development of the contract, after which development the contract might be submitted to a second application (e.g., DocuSign) to facilitate execution (e.g., signing) of the contract. In this case, the SalesForce and DocuSign applications might be registered with the content management system to facilitate authorized access to the sales contract document managed (e.g., stored, updated, etc.) at the content management system.

An inter-application data management framework is established at the content management system to interrelate certain sets of interactions performed over the applications (step 216). Frameworks, such as the inter-application data management framework or any other framework discussed herein, are sets of computing entities that cooperatively facilitate various data collection and data distribution functions. The computing entities of a framework might comprise various data structures, application programming interfaces (APIs), communication protocols, authentication protocols, and/or other entities. At least some of the entities of a framework are often strictly designed to facilitate a certain function or certain set of functions. For example, an embodiment of the inter-application data management framework described herein might specify that one or more link attributes are to be included in API calls and/or certain data records to facilitate the aforementioned linking between applications. Other entities of a framework might be designed to offer flexibility. For example, an embodiment of the inter-application data management framework described herein might comprise specialized data structures that facilitate enterprise-specific definitions of workflows, interactions, or metrics.

As depicted in ongoing operations 220, any interaction events corresponding to interactions over the content objects performed by the applications are recorded (step 222). Referring to the aforementioned example, certain APIs and/or data structures of the inter-application data management framework might be used to record event attributes associated with interaction events invoked at the SalesForce and DocuSign applications. At certain moments in time, sets of interaction events are selected, which selected sets comprise events from two or more applications (step 224). For example, a set of interaction events associated with one or more link attributes (e.g., project name, customer name, workflow name, document name, etc.) might be selected in response to a request for performance measurements associated with those link attributes. One or more inter-application performance measurements pertaining to the sets of interaction events are generated (step 226). As an example, inter-application performance measurements that pertain to interaction events from respective workflows are generated.

Various event attributes and/or other attributes (e.g., metric definition attributes, etc.) associated with the sets of interaction events might be analyzed to generate the inter-application performance measurements. The inter-application performance measurements are then presented to one or more users (step 228). For example, at least some of the measurements might be visually presented in text and/or graphics at user interfaces accessible by the users.

One embodiment of a system, data flows, and data structures for implementing the inter-application workflow performance analysis technique 200 and/or other herein disclosed techniques is disclosed as follows.

Figure 3:
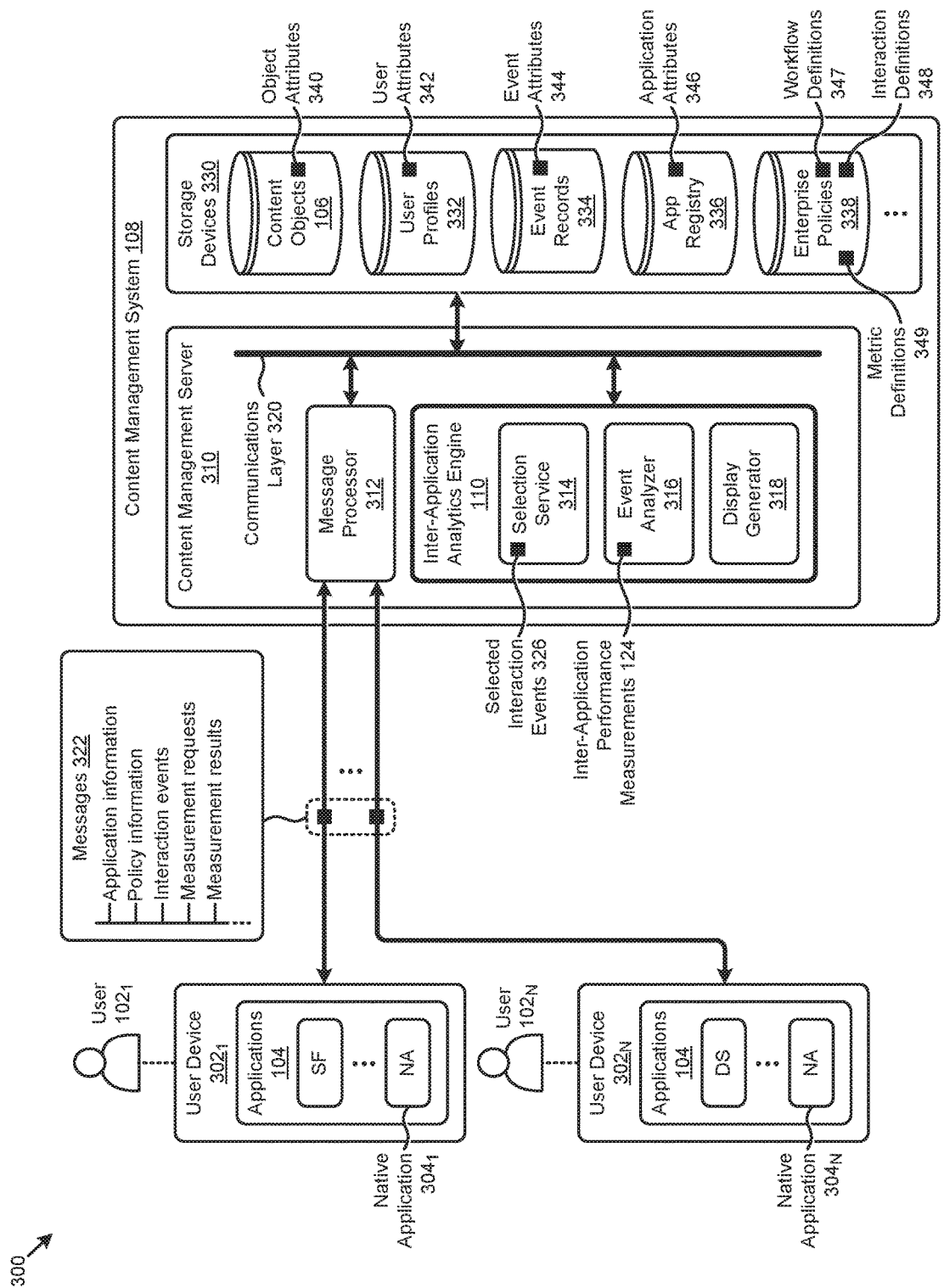
FIG. 3 is a block diagram of a system that measures the performance of workflows performed over multiple applications, according to an embodiment.

FIG. 3 is a block diagram of a system 300 that measures the performance of workflows performed over multiple applications. As an option, one or more variations of system 300 or any aspect thereof may be implemented in the context of the architecture and functionality of the embodiments described herein. The system 300 or any aspect thereof may be implemented in any environment.

FIG. 3 illustrates aspects pertaining to linking content object interactions that are performed across multiple applications so as to generate performance measurements of workflows that comprise the interactions. Specifically, the figure is being presented to show one embodiment of certain representative components and associated data structures and data flows implemented in a computing environment to facilitate the herein disclosed techniques. As shown, the components, data flows, and data structures are associated with a set of users (e.g., user $102_1$, . . . , user $102_N$) that interact with each other and a set of content objects 106 managed at a content management system 108. The components, data flows, and data structures shown in FIG. 3 present one partitioning and associated data manipulation approach. The specific example shown is purely exemplary, and other subsystems, data structures, and/or partitionings are reasonable.

As shown, system 300 comprises an instance of content management server 310 operating at content management system 108. Content management server 310 comprises a message processor 312 and an instance of an inter-application analytics engine 110, which comprises a selection service 314, an event analyzer 316, and a display generator 318. A plurality of instances of the foregoing components might operate at a plurality of instances of servers (e.g., content management server 310) at content management system 108 and/or any portion of system 300. Such instances can interact with a communications layer 320 to access each other and/or a set of storage devices 330 that store various information to support the operation of the components of system 300 and/or any implementations of the herein disclosed techniques.

For example, the servers and/or storage devices of content management system 108 might facilitate interactions over content objects 106 by the users (e.g., user $102_1$, . . . , user $102_N$) from a respective set of user devices (e.g., user device $302_1$, . . . , user device $302_N$). A content management system "manages" a plurality of content objects at least in part by maintaining (e.g., storing, updating, resolving interaction conflicts, etc.) the content objects subject to the various interactions performed over the content objects by users of the content objects at their respective user devices. The content objects (e.g., files, folders, etc.) in content objects 106 are characterized at least in part by a set of object attributes 340 (e.g., content object metadata) stored at storage devices 330. Furthermore, the users are characterized at least in part by a set of user attributes 342 stored in a set of user profiles 332 at storage devices 330.

The users access instances of applications 104 at their respective user devices to interact with content objects 106 managed by content management system 108. As shown, the applications can comprise instances of native applications (e.g., native application $304_1$, ..., native application $304_N$) or instances of third-party applications (e.g., a SalesForce or "SF" application, a DocuSign or "DS" application, etc.). Various information pertaining to integrations of such third-party applications with content management system 108 are normalized and then codified for storage in an app registry 336, which in turn is maintained as data in storage devices 330. At least some information of app registry 336 is organized according to an inter-application data management framework as earlier described. In some cases, certain portions of the information in app registry 336 might be locally accessible at the user devices by the third-party applications. For example, a first local app registry might be accessible by app "SF" at user device $302_1$ and a second local app registry might be accessible by app "DS" at user device $302_N$.

The instances of the applications operating at the user devices send or receive various instances of messages 322 that are received or sent by message processor 312 at content management server 310. In some cases, messages 322 are sent to or received from content management server 310 without human interaction. One class of messages 322 corresponds to application-specific information received at content management system 108 in response to executing application integration operations. For example, instances of application attributes 346 that correspond to a particular application might be issued by an enterprise and stored in app registry 336 when the application is registered with content management system 108. Select users (e.g., system administrators) at enterprises may also submit certain policy information and/or other enterprise-specific information in instances of messages 322. Such enterprise-specific policy information is stored in a set of enterprise policies 338 at storage devices 330. As shown, enterprise policies 338 might comprise instances of workflow definitions 347, interaction definitions 348, metric definitions 349, and/or other information that can be accessed to facilitate the herein disclosed techniques. As used herein, an enterprise-specific policy is any information that identifies and/or governs the use of workflows, and/or information that identifies or characterized tasks of the workflows, and/or information that pertains to metrics to be considered when generating performance measurements.

Another class of messages 322 corresponds to interaction events that are invoked by the users when they interact with one another (e.g., user-to-user interactions) and/or when users interact with various content objects (e.g., user-to-content interactions). As described herein, the interactions can be performed at any of the instances of applications 104 (e.g., native applications, third-party applications, etc.). As examples, the users might log in to their respective instances of a native application or any third-party applications to interact with content objects that they own or that are shared with them to invite other users to collaborate on content objects and/or to perform other collaboration activities. Any of the foregoing interactions or collaboration activities can be characterized by one or more interaction events.

The message processor 312 at content management server 310 monitors the messages 322 to detect interaction event messages that correspond to interaction events performed over the plurality of content objects at the plurality of applications. Message processor 312 codifies certain event attributes 344 pertaining to the interaction events in a set of event records 334 stored in storage devices 330. In some cases, message processor 312 will retrieve other attributes (e.g., user attributes 342, object attributes 340, application attributes 346, interaction definition attributes, etc.) to facilitate populating the event records 334.

At certain moments in time, instances of messages 322 comprising measurement requests are received at message processor 312. Such requests are issued to retrieve one or more inter-application performance measurements from content management system 108. For example, user $102_1$ might load a performance dashboard view in native application $304_1$ that invokes one or more measurement requests to facilitate population of the dashboard view. In response to receiving measurement requests, inter-application analytics engine 110 accesses the selection service 314 to select respective sets of selected interaction events 326 from event records 334 in accordance with request attributes associated with the requests. As an example, consider a measurement request that includes a link attribute that identifies a particular customer. In this case, the customer identifier and/or other attributes might be included in a query of event records 334 to select a set of interaction events that are associated with the customer.

The event analyzer 316 is then called to analyze the event attributes that constitute the selected interaction events 326 to generate one or more instances of inter-application performance measurements 124. The inter-application performance measurements 124 generated by event analyzer 316 will often be based at least in part on other data available at content management system 108, such as certain data stored in enterprise policies 338 and/or app registry 336.

The inter-application performance measurements 124 are accessed by the display generator 318 to prepare the measurements for presentation. Specifically, display generator 318 generates the user interface display elements that comprise an active, visual presentation of the inter-application performance measurements 124 and/or other information. Such user interface display elements might comprise data tables, charts, graphs, and/or other human-readable elements. The user interface display elements and other information associated with the inter-application performance measurements 124 are codified into instances of messages 322 which are in turn delivered to the users. As an example, instances of user interface display elements that describe various inter-application performance measurements are dynamically generated and presented to respective users in their corresponding instances of a native application.

A detailed embodiment of the inter-application data management framework described herein is disclosed as follows.

Figure 4:
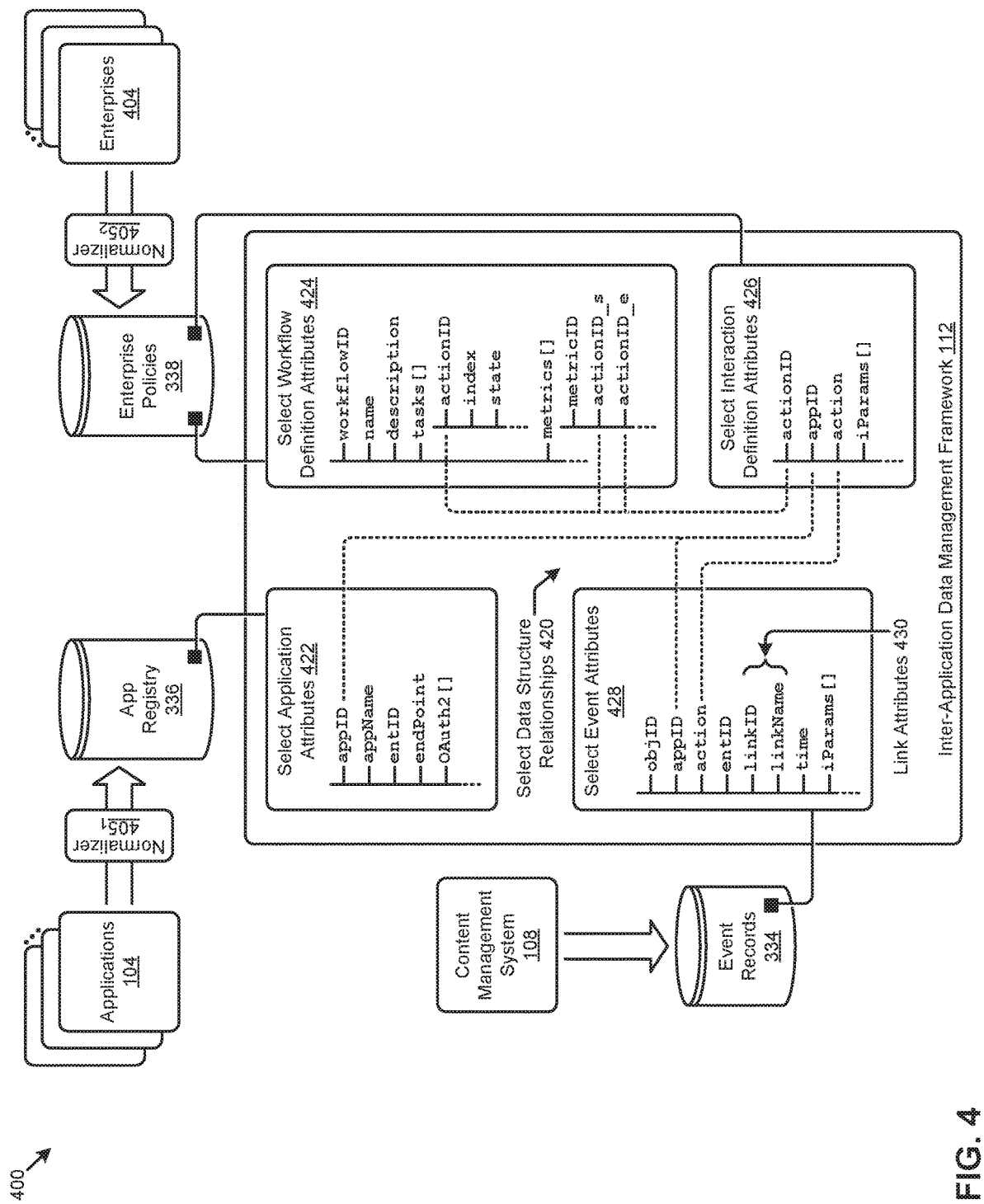
FIG. 4 illustrates an inter-application data management technique as used to measure the performance of workflows performed over multiple applications, according to an embodiment.

FIG. 4 illustrates an inter-application data management technique 400 as used to measure the performance of workflows performed over multiple applications. As an option, one or more variations of inter-application data management technique 400 or any aspect thereof may be implemented in the context of the architecture and functionality of the embodiments described herein. The inter-application data management technique 400 or any aspect thereof may be implemented in any environment.

FIG. 4 illustrates aspects pertaining to linking content object interactions that are performed across multiple applications so as to generate performance measurements of workflows that comprise the interactions. Specifically, the figure presents certain specialized data structures for organizing and/or storing various data to facilitate the aforementioned inter-application linking and other techniques disclosed herein. As shown, the data structures are associated with the inter-application data management framework 112 earlier described.

These data structures and other data structures discussed herein are configured to improve the way a computer stores and retrieves certain data in memory when performing the herein disclosed techniques. Data can be organized and/or stored in accordance with these data structures using various techniques. For example, the representative data structures associated with inter-application data management framework 112 shown in FIG. 4 indicate that the constituent data of the data structures might be organized and/or stored in a tabular structure (e.g., relational database table) that has rows that relate various attributes with a particular data entity. As another example, the underlying data might be organized and/or stored in a programming code object that has instances corresponding to a particular data entity and properties corresponding to the various attributes associated with the data entity. A representative set of select data structure relationships 420 between certain data entities are also shown.

When instances of applications 104 (e.g., third-party applications) are integrated (e.g., registered) with a content management system 108, respective sets of application-specific information are populated in an app registry 336. Moreover, instances of enterprises 404 that have access to content management system 108 populate respective instances of enterprise policies 338 with enterprise-specific information. The data structures of app registry 336 and enterprise policies 338 are defined by the inter-application data management framework 112 to facilitate the herein disclosed techniques.

As shown, the system supports a plurality of applications 104 as well as a plurality of enterprises 404. As such, data that is stored in the app registry 336 and/or data that is stored in enterprise policies may be normalized so as to facilitate comparisons and other processing in spite of a plurality of origins and formats of incoming data. For example, a first application of the applications 104 might refer to its "application ID" as a number, whereas a second application of the applications 104 might refer to its "application ID" as a character string. A normalizer (e.g., $405_1$) might recode these different representations into a common representation. As another example, a first app might refer to an event raised at or by particular enterprise using an app-specific ID (e.g., "entID" of the select event attributes 428) whereas a second app might refer to a different event raised at or by the same particular enterprise using a different app-specific ID (e.g., "entID" of the select event attributes 428). In this and other cases, a correspondence between a first occurrence of an "entID" and a second of an "entID" is maintained. As such, when "entID"s or other metadata entries that are different as between apps, but the different "entID"s or other metadata nevertheless refer to the same attribute the occurrence of events can be normalized or otherwise mapped so as to reflect that different events processed by different apps refer to the same attribute. In some cases, the normalization processing of normalizer $405_1$ creates and manages a plurality of maps, each of which maps relate incoming data (e.g., from the applications 104) to an internal representation. For example, in a first map or map entry, the attribute value "Enterprise1" might be mapped to "CustomerA", and in a second map or map entry, the attribute value "Enterprise2" might be also mapped to "CustomerA". As such, variations that may occur in the representation of any attribute in any particular app can be normalized into a comment representation.

Similarly, data that is stored in the enterprise policies 338 may be normalized so as to facilitate comparisons and other processing in spite of a plurality of origins and formats of incoming data. For example, a first enterprise of the enterprises 404 might refer to its "workflow ID" as a number, whereas a second enterprise of the enterprises 404 might refer to its "workflow ID" as a character string. A normalizer (e.g., $405_2$) might recode these different representations into a common representation. In some cases, the normalization processing of normalizer $405_2$ creates and manages a plurality of maps, each of which maps relate incoming data (e.g., from the enterprises 404) to an internal representation which is in turned used by operational elements of the system.

Further details regarding general approaches to handling content object metadata and/or other types of metadata are described in U.S. application Ser. No. 16/553,144 titled "EXTENSIBLE CONTENT OBJECT METADATA", filed on Aug. 27, 2019, which is hereby incorporated by reference in its entirety.

The content management system 108 also stores instances of event records 334 in accordance with the data structures of the inter-application data management framework 112. Data stored in the data structures of the inter-application data management framework 112 may be normalized so as to facilitate comparisons. For example, one data item might refer to units of time or durations as a number of days, whereas another data item might refer units of time or durations as a number of hours. For comparison purposes, days can be normalized to a number and/or fraction of hours, or, for comparison purposes, hours can be normalized to a number and/or fraction of days.

In some cases, certain portions of the aforementioned data structures and/or data stores are populated in response to various inputs (e.g., selections, entered text, etc.) received from system administrators and/or application developers in response to interactions with various user interfaces (e.g., admin and/or developer console). For example, an application developer might first register a set of applications, then a system administrator might define certain interactions that are performed at the applications. The system administrator might also define various workflows and/or workflow performance metrics that pertain to combinations of the foregoing interactions.

Additionally or alternatively, various techniques may be employed to automatically determine various workflows that might pertain to combinations of the foregoing interactions.

Further details regarding general approaches to automatically determining workflows are described in U.S. application Ser. No. 16/553,161 titled "WORKFLOW SELECTION", filed on Aug. 27, 2019, which is hereby incorporated by reference in its entirety.

As indicated in a set of select application attributes 422, each of the applications that are registered with the content management system is identified by an application identifier (e.g., stored in an "appID" field), an application name (e.g., stored in an "appName" field), an enterprise identifier (e.g., stored in an "entID" field), an endpoint URL (e.g., stored in an "endpoint" field), a set of OAuth2 credentials (e.g., stored in an "OAuth2[ ]" object), and/or other attributes. As can be observed, the application identifier or "appID" is referenced by other data structures to associate the data underlying those structures with a particular application. Certain attributes (e.g., "entID", "endpoint", etc.) from select application attributes 422 might be included in interaction event messages issued from the applications to facilitate identification of the particular instances of the application or applications that issued the messages.

Such interaction event messages may also identify one or more interactions as defined by a set of select interaction definition attributes 426. As can be observed, an interaction associated with an application identified in an "appID" field is defined by an interaction identifier (e.g., stored in an "actionID" field), an interaction type description (e.g., stored in an "action" field), a set of interaction parameters specific to the interaction (e.g., stored in an "iParams[ ]" object), and/or other attributes. In some embodiments, an interaction identifier (e.g., "SF.create") might be constructed from the application identifier (e.g., "SF") and the interaction type description (e.g., "create").

Various workflows are also defined in the inter-application data management framework 112 in accordance with a data structure described by a set of select workflow definition attributes 424. Specifically, a particular workflow is defined by a workflow identifier (e.g., stored in a "workflowID" field), a workflow name (e.g., stored in a "name" field), a workflow description (e.g., stored in a "description" field), a set of tasks associated with the workflow (e.g., stored in a "tasks [ ]" object), a set of metrics associated with the workflow (e.g., stored in a "metrics [ ]" object), and/or other attributes. As shown, each task of the workflow is described by an interaction identifier (e.g., stored in an "actionID" field), a task sequence index (e.g., stored in an "index" field), a task state description (e.g., stored in a "state" field), and/or other attributes. Also as shown each metric associated with the workflow is described by a metric identifier (e.g., stored in a "metricID" field), an interaction identifier that signals the start event of the metric (e.g., stored in an "actionID_s" field), an interaction identifier that signals the end event of the metric (e.g., stored in an "actionID_e" field), and/or other attributes.

As indicated in a set of select event attributes 428, each event record stored in event records 334 comprises an object identifier (e.g., stored in an "objID" field), an application identifier (e.g., stored in an "appID" field), an interaction type description (e.g., stored in an "action" field), an enterprise identifier (e.g., stored in an "entID" field), a link identifier (e.g., stored in a "linkID" field), a link name (e.g., stored in a "linkName" field), a timestamp (e.g., stored in a "time" field), one or more interaction parameters specific to the interaction event (e.g., stored in an "iParams[ ]" object), and/or other attributes. As can be observed, the link identifier and/or the link name and/or other attributes can constitute a set of link attributes 430 that facilitate the linking of interactions over content objects performed over multiple heterogeneous applications.

The foregoing discussion includes techniques for recording interaction events associated with interactions over content objects performed at multiple heterogeneous applications (e.g., step 222 of FIG. 2), which techniques are disclosed in further detail as follows.

Figure 5:
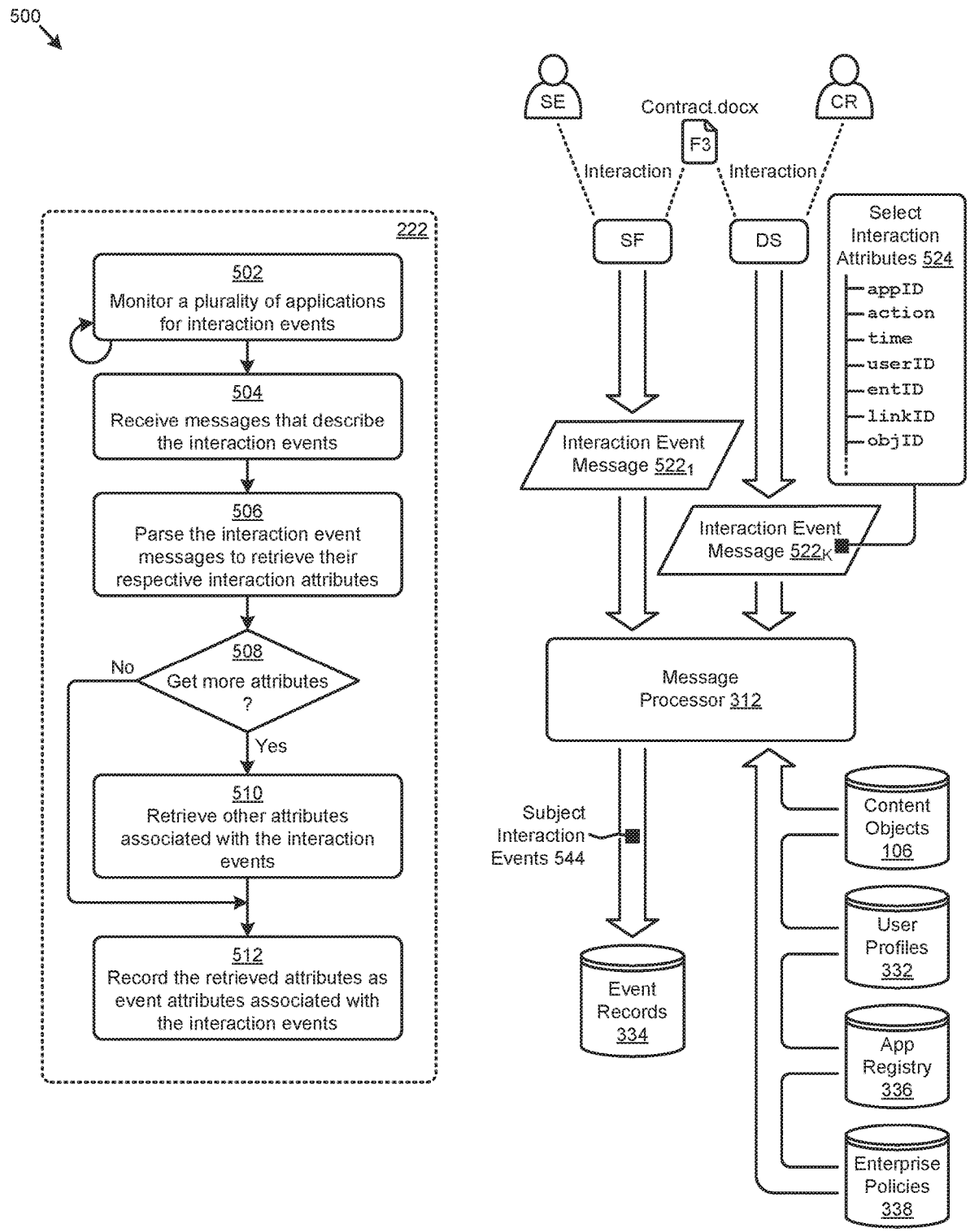
FIG. 5 presents an interaction event recording technique as implemented in systems that facilitate measuring the performance of workflows performed over multiple applications, according to an embodiment.

FIG. 5 presents an interaction event recording technique 500 as implemented in systems that facilitate measuring the performance of workflows performed over multiple applications. As an option, one or more variations of interaction event recording technique 500 or any aspect thereof may be implemented in the context of the architecture and functionality of the embodiments described herein. The interaction event recording technique 500 or any aspect thereof may be implemented in any environment.

FIG. 5 illustrates aspects pertaining to linking content object interactions that are performed across multiple applications so as to generate performance measurements of workflows that comprise the interactions. Specifically, the figure is presented to illustrate one embodiment of certain steps and/or operations that facilitate recording interaction events performed over content objects at various heterogeneous applications. As depicted in the figure, the steps and/or operations are associated with step 222 of FIG. 2. A representative scenario is also shown in the figure to illustrate an example application of interaction event recording technique 500.

The interaction event recording technique 500 commences by monitoring a plurality of applications for interaction events (step 502). As illustrated, an instance of message processor 312 may continuously listen or poll for interaction events performed at a plurality of applications that includes an instance of app "SF" accessed by user "SE" and an instance of app "DS" accessed by user "CR". When interaction event messages are received (step 504), the interaction event messages are parsed to retrieve respective sets of interaction attributes from the messages (step 506). As shown, message processor 312 receives an interaction event message $522_1$ in response to user "SE" interacting with file "F3" at app "SF" and receives an interaction event message $522_K$ in response to user "CR" interacting with file "F3" at app "DS". As indicated by a set of select interaction attributes 524, the interaction attributes associated with the interaction event messages include an application identifier (e.g., stored in an "appID" field), an interaction type description (e.g., stored in an "action" field), a timestamp (e.g., stored in a "time" field), a user identifier (e.g., stored in a "userID" field), an enterprise identifier (e.g., stored in an "entID" field), a link identifier (e.g., stored in a "linkID" field), a content object identifier (e.g., stored in an "objID" field), and/or other attributes.

If other attributes are to be considered ("Yes" path of decision 508), then various other attributes associated with the interaction event messages are retrieved (step 510). In this case, message processor 312 might access the datastores of content objects 106, user profiles 332, app registry 336, enterprise policies 338, and/or other data sources to retrieve certain attributes associated with the interaction attributes of the interaction event messages.

All retrieved attributes are then recorded as event attributes associated with the interaction event message (step 512). As stated, if other attributes are to be considered ("Yes" path of decision 508), the event attributes comprise some or all of the retrieved interaction attributes and the retrieved other attributes. If merely the interaction attributes are considered ("No" path of decision 508), the event attributes comprise some or all of the retrieved interaction attributes. In the shown scenario, message processor 312 stores in event records 334 sets of event attributes that correspond to a respective set of subject interaction events 544 described by interaction event message $522_1$ and interaction event message $522_K$.

The foregoing discussion includes techniques for selecting and analyzing such sets of interaction events associated with two or more applications to generate inter-application performance measurements (e.g., step 224 and step 226 of FIG. 2), which techniques are disclosed in further detail as follows.

Figure 6:
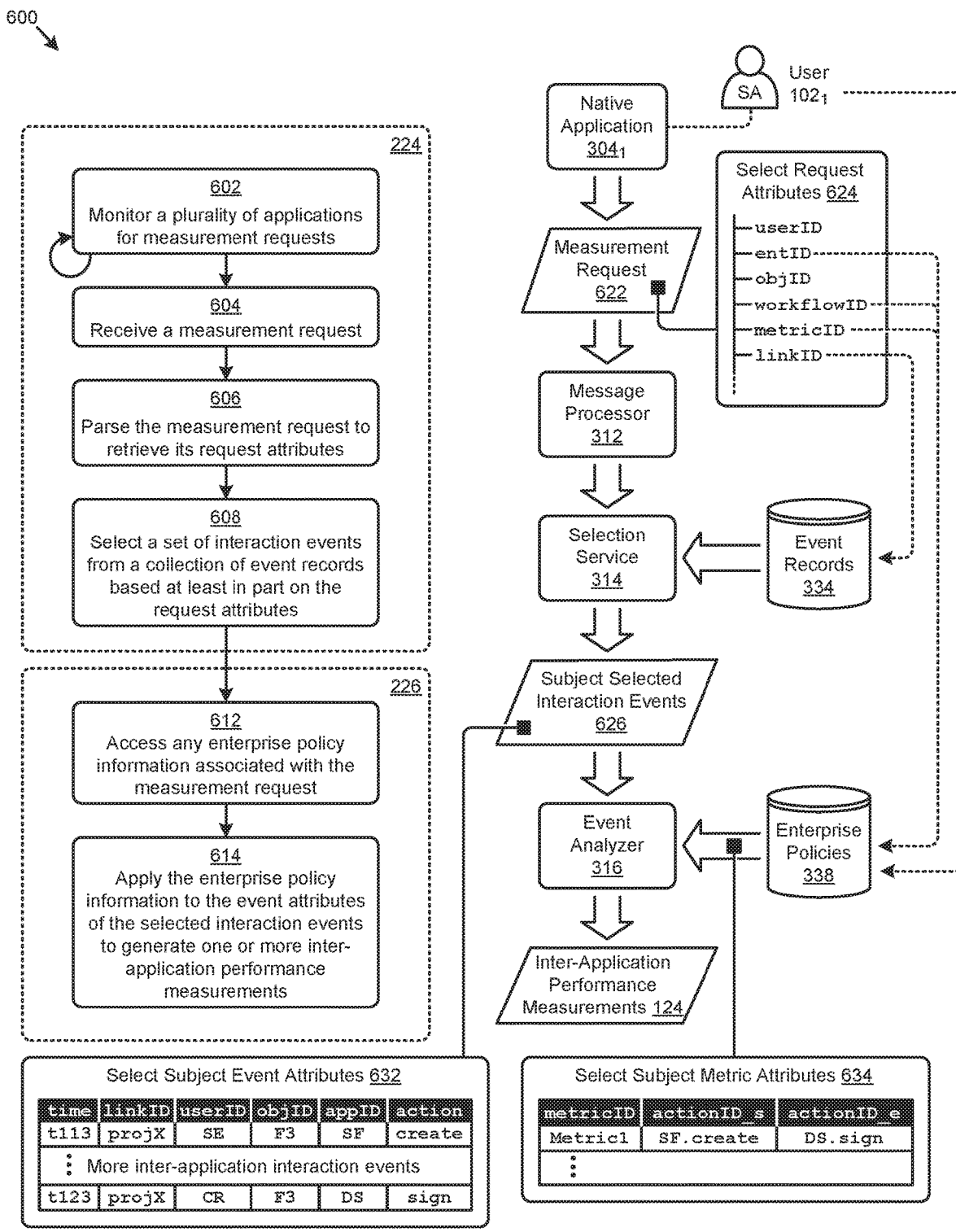
FIG. 6 presents a workflow performance measurement technique as implemented in systems that facilitate measuring the performance of workflows performed over multiple applications, according to an embodiment.

FIG. 6 presents a workflow performance measurement technique 600 as implemented in systems that facilitate measuring the performance of workflows performed over multiple applications. As an option, one or more variations of workflow performance measurement technique 600 or any aspect thereof may be implemented in the context of the architecture and functionality of the embodiments described herein. The workflow performance measurement technique 600 or any aspect thereof may be implemented in any environment.

FIG. 6 illustrates aspects pertaining to linking content object interactions that are performed across multiple applications so as to generate performance measurements of workflows that comprise the interactions. Specifically, the figure is presented to illustrate one embodiment of certain steps and/or operations that facilitate selecting and analyzing sets of interaction events associated with two or more applications to generate inter-application performance measurements. As depicted in the figure, the steps and/or operations are associated with step 224 and step 226 of FIG. 2. A representative scenario is also shown in the figure to illustrate an example application of workflow performance measurement technique 600.

The workflow performance measurement technique 600 commences by monitoring a plurality of applications for measurement requests (step 602). As illustrated, an instance of message processor 312 may continuously listen or poll for measurement requests issued from applications to retrieve various inter-application workflow performance measurements. When a measurement request is received (step 604), the request is parsed to retrieve its request attributes (step 606). For example, message processor 312 might receive a measurement request 622 issued from native application 304$_1$ by user 102$_1$ (e.g., a system administrator or "SA"). As indicated by a set of select request attributes 624, the request attributes associated with measurement request 622 or any measurement request include a user identifier (e.g., stored in a "userID" field), an enterprise identifier (e.g., stored in an "entID" field), a content object identifier (e.g., stored in an "objID" field), a workflow identifier (e.g., stored in a "workflowID" field), a metric identifier (e.g., stored in a "metricID" field), a link identifier (e.g., stored in a "linkID" field), and/or other attributes.

A set of interaction events are selected based at least in part on the request attributes (step 608). As an example, message processor 312 forwards the request attributes extracted from measurement request 622 to an instance of a selection service 314. The selection service 314 uses one or more of the request attributes (e.g., the link attribute) to query the event records 334 to select a set of subject selected interaction events 626 that pertain to the measurement request.

To facilitate processing of the selected interaction events, any enterprise policy information associated with the measurement request are accessed (step 612). As shown, an instance of an event analyzer 316 might use certain request attributes (e.g., enterprise identifier, workflow identifier, metric identifier, etc.) to retrieve any relevant enterprise policy information from a store of enterprise policies 338. The enterprise policy information is applied to the event attributes associated with the selected interaction events to determine one or more inter-application performance measurements (step 614). In some cases, the enterprise policy information includes content object access information. For example, enterprise policy information might allow or deny access to a content object by a particular user. Furthermore, such enterprise policy information might allow or deny access to any actions taken over a particular content object by a particular user. As such it can happen that a particular user many not be able to see measurements that derive from events that are not accessible (e.g., access denied) to that particular user.

In the illustrated scenario, event analyzer 316 applies the enterprise policy information retrieved from enterprise policies 338 to the event attributes of subject selected interaction events 626 to generate a particular inter-application performance measurement. In the specific example shown, event analyzer 316 generates a performance measurement for metric "Metric1" from interaction events performed over two or more applications (e.g., app "SF" and app "DS") that are linked by a "ProjX" link identifier. As shown, the events are linked by the "ProjX" link identifier that appears in multiple timestamped instances of the select subject event attributes 632. Still further, the action "create" and the action "sign" are interrelated by the data structure shown as select subject metric attributes 634.

Considering that the "Metric1" start event is indicated by a "create" action at app "SF" and that the "Metric1" end event is indicated by a "sign" action at app "DS", a measurement for "Metric1" might be equal to 10 (e.g., "t123"-"t113") time units (e.g., days).

As can be understood from the foregoing discussion, the metrics are not generic hardware-centric metrics such as CPU utilization or memory usage, but rather are metrics that pertain to the usage of a particular application and/or that pertain to operations that are performed cooperatively between two or more heterogeneous applications.

The foregoing discussions include techniques for presenting the inter-application performance measurements to various users (e.g., step 228 of FIG. 2), which techniques are disclosed in further detail as follows.

Figure 7:
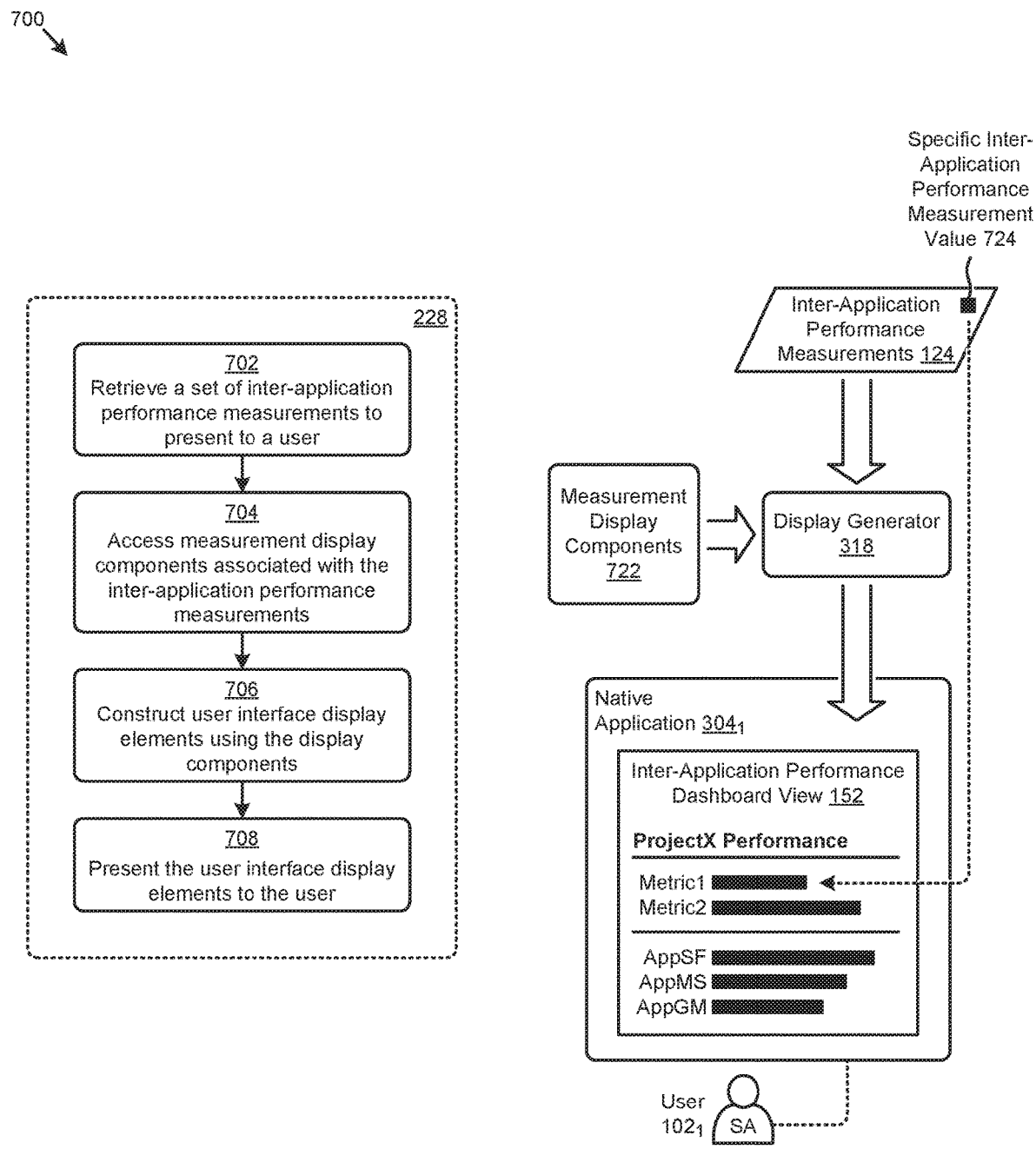
FIG. 7 presents a workflow performance analytics presentation technique as implemented in systems that facilitate measuring the performance of workflows performed over multiple applications, according to an embodiment.

FIG. 7 presents a workflow performance analytics presentation technique 700 as implemented in systems that facilitate measuring the performance of workflows performed over multiple applications. As an option, one or more variations of workflow performance analytics presentation technique 700 or any aspect thereof may be implemented in the context of the architecture and functionality of the embodiments described herein. The workflow performance analytics presentation technique 700 or any aspect thereof may be implemented in any environment.

FIG. 7 illustrates aspects pertaining to linking content object interactions that are performed across multiple applications so as to generate performance measurements of workflows that comprise the interactions. Specifically, the figures are presented to illustrate one embodiment of certain steps and/or operations that facilitate presenting inter-application performance measurements to a user. As depicted in the figure, the steps and/or operations are associated with step 228 of FIG. 2. A representative scenario is also shown in the figures to illustrate an example application of workflow performance analytics presentation technique 700.

The workflow performance analytics presentation technique 700 commences by retrieving a set of inter-application performance measurements to present to a user (step 702). As illustrated, an instance of display generator 318 might retrieve a set of inter-application performance measurements 124. A set of measurement display components associated with the inter-application performance measurements is accessed (step 704). As shown, display generator 318 accesses a set of measurement display components 722 to identify certain components (e.g., chart types, style sheets, etc.) associated with inter-application performance measurements 124. For example, horizontal bar charts might be identified as the chart type for the measurements.

Certain user interface display elements are constructed from the display components and the inter-application performance measurements (step 706). As an example, display generator 318 might access a user interface library (e.g., React library) to generate the code for rendering the display components of inter-application performance measurements 124 and other related information at a target user interface. The user interface display elements are then presented to the user at the target user interface (step 708). As illustrated, the user interface display elements associated with inter-application performance measurements 124 are presented in an inter-application performance dashboard view 152 at native application $304_1$ associated with user $102_1$. Specifically shown in inter-application performance dashboard view 152 is a graphical visualization of a specific inter-application performance measurement value 724 that corresponds to "Metric1".

Additional Embodiments of the Disclosure

Additional Practical Application Examples

Figure 8A:
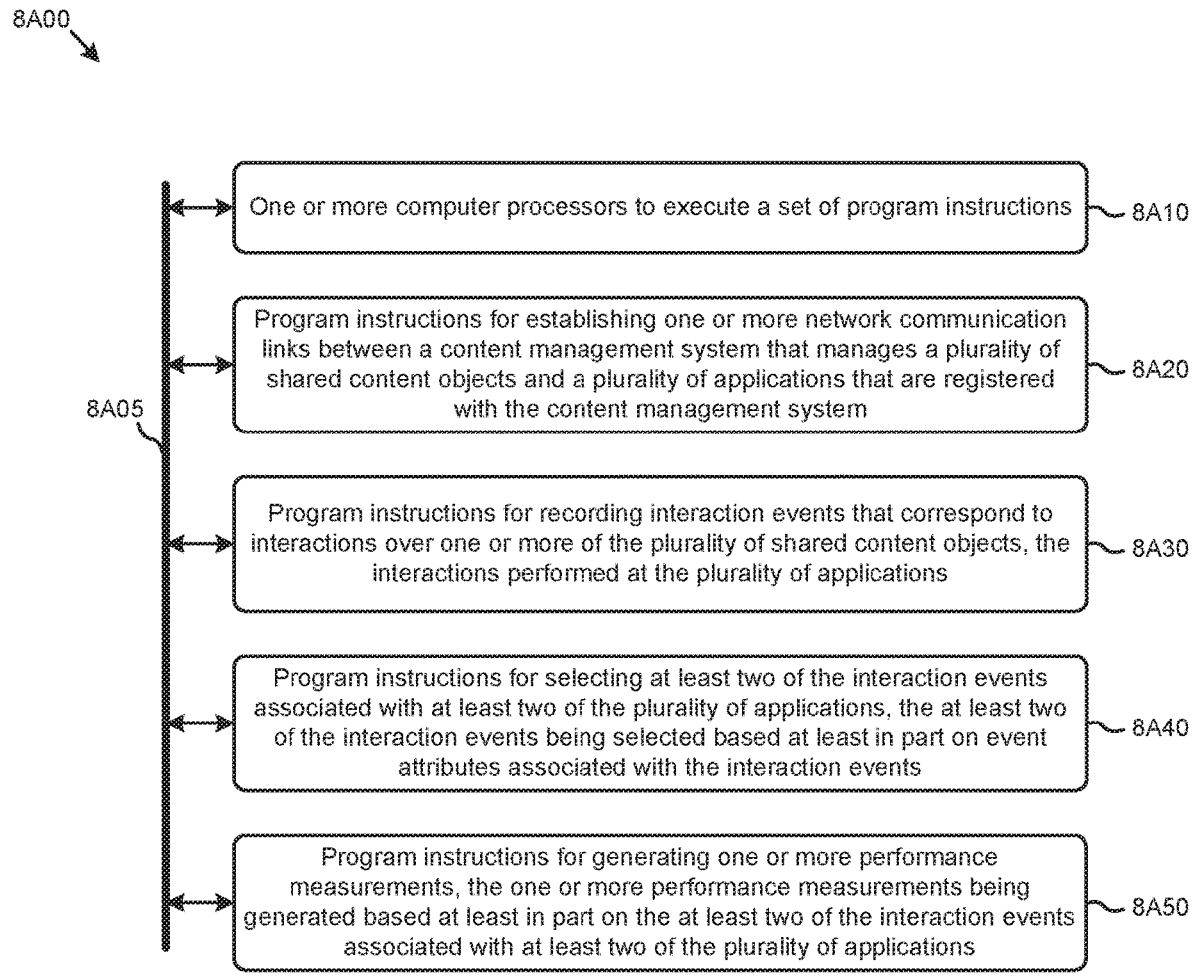
FIG. 8A and FIG. 8B depict system components as arrangements of computing modules that are interconnected so as to implement certain of the herein-disclosed embodiments.

FIG. 8A depicts a system 8A00 as an arrangement of computing modules that are interconnected so as to operate cooperatively to implement certain of the herein-disclosed embodiments. This and other embodiments present particular arrangements of elements that, individually or as combined, serve to form improved technological processes that address measuring the performance of workflows performed over multiple applications. The partitioning of system 8A00 is merely illustrative and other partitions are possible. As an option, the system 8A00 may be implemented in the context of the architecture and functionality of the embodiments described herein. Of course, however, the system 8A00 or any operation therein may be carried out in any desired environment. The system 8A00 comprises at least one processor and at least one memory, the memory serving to store program instructions corresponding to the operations of the system. As shown, an operation can be implemented in whole or in part using program instructions accessible by a module. The modules are connected to a communication path 8A05, and any operation can communicate with any other operations over communication path 8A05. The modules of the system can, individually or in combination, perform method operations within system 8A00. Any operations performed within system 8A00 may be performed in any order unless as may be specified in the claims. The shown embodiment implements a portion of a computer system, presented as system 8A00, comprising one or more computer processors to execute a set of program code instructions (module 8A10) and modules for accessing memory to hold program code instructions to perform: establishing one or more network communication links between a content management system that manages a plurality of shared content objects and a plurality of applications that are registered with the content management system (module 8A20); recording interaction events that correspond to interactions over one or more of the plurality of shared content objects, the interactions performed at the plurality of applications (module 8A30); selecting at least two of the interaction events associated with at least two of the plurality of applications, the at least two of the interaction events being selected based at least in part on event attributes associated with the interaction events (module 8A40); and generating one or more performance measurements, the one or more performance measurements being generated based at least in part on the at least two of the interaction events associated with at least two of the plurality of applications (module 8A50).

Variations of the foregoing may include more or fewer of the shown modules. Certain variations may perform more or fewer (or different) steps and/or certain variations may use data elements in more, or in fewer, or in different operations. Still further, some embodiments include variations in the operations performed, and some embodiments include variations of aspects of the data elements used in the operations.

Figure 8B:
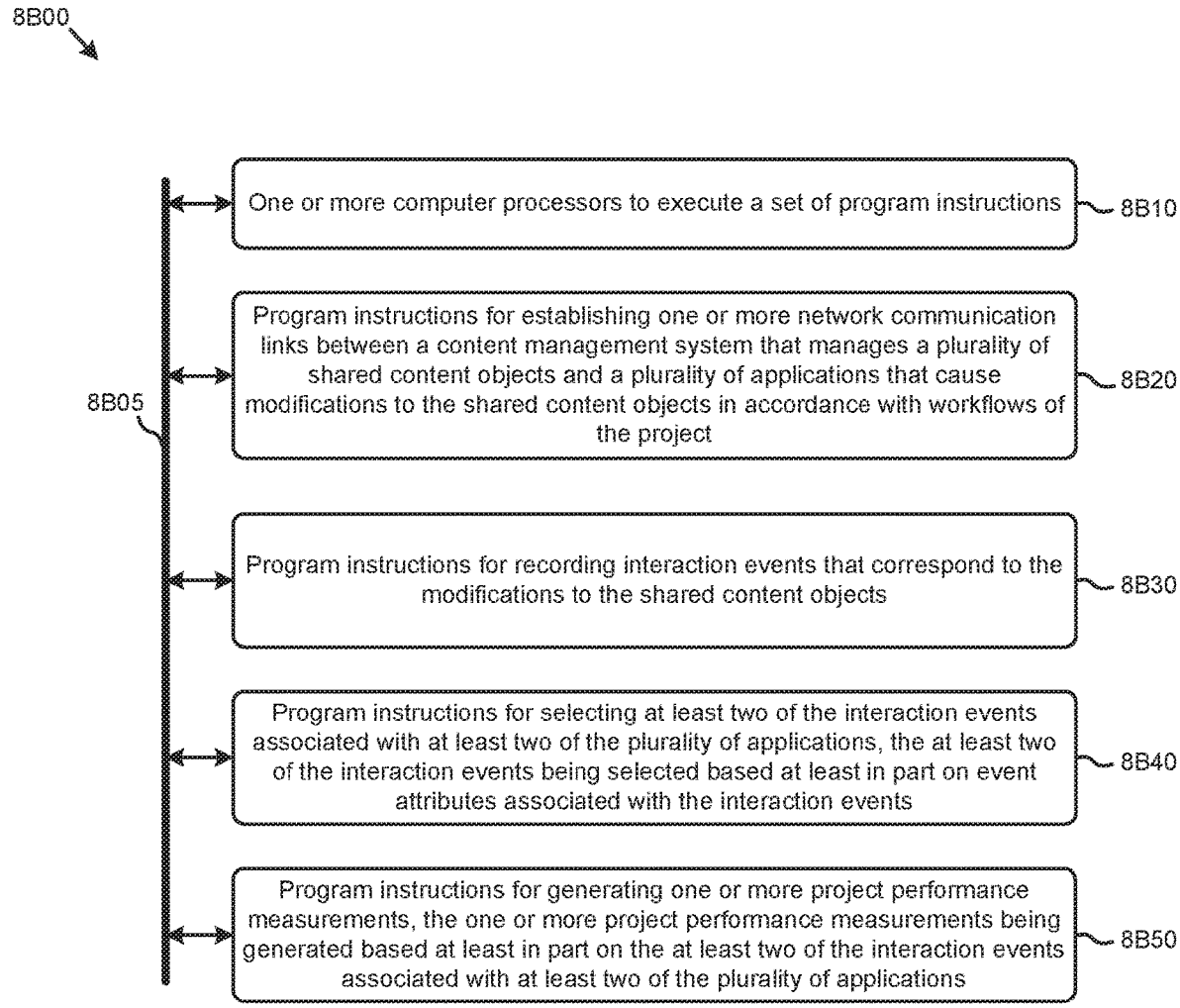

FIG. 8B depicts a system 8B00 as an arrangement of computing modules that are interconnected so as to operate cooperatively to implement certain of the herein-disclosed embodiments. The partitioning of system 8B00 is merely illustrative and other partitions are possible. As an option, the system 8B00 may be implemented in the context of the architecture and functionality of the embodiments described herein. Of course, however, the system 8B00 or any operation therein may be carried out in any desired environment. The system 8B00 comprises at least one processor and at least one memory, the memory serving to store program instructions corresponding to the operations of the system. As shown, an operation can be implemented in whole or in part using program instructions accessible by a module. The modules are connected to a communication path 8B05, and any operation can communicate with any other operations over communication path 8B05. The modules of the system can, individually or in combination, perform method operations within system 8B00. Any operations performed within system 8B00 may be performed in any order unless as may be specified in the claims. The shown embodiment implements a portion of a computer system, presented as system 8B00, comprising one or more computer processors to execute a set of program code instructions (module 8B10) and modules for accessing memory to hold program code instructions to perform: establishing one or more network communication links between a content management system that manages a plurality of shared content objects and a plurality of applications that cause modifications to the shared content objects in accordance with workflows of the project (module 8B20); recording interaction events that correspond to the modifications to the shared content objects (module 8B30); selecting at least two of the interaction events associated with at least two of the plurality of applications, the at least two of the interaction events being selected based at least in part on event attributes associated with the interaction events (module 8B40); and generating one or more project performance measurements, the one or more project performance measurements being generated based at least in part on the at least two of the interaction events associated with at least two of the plurality of applications (module 8B50).

System Architecture Overview

Additional System Architecture Examples

Figure 9A:
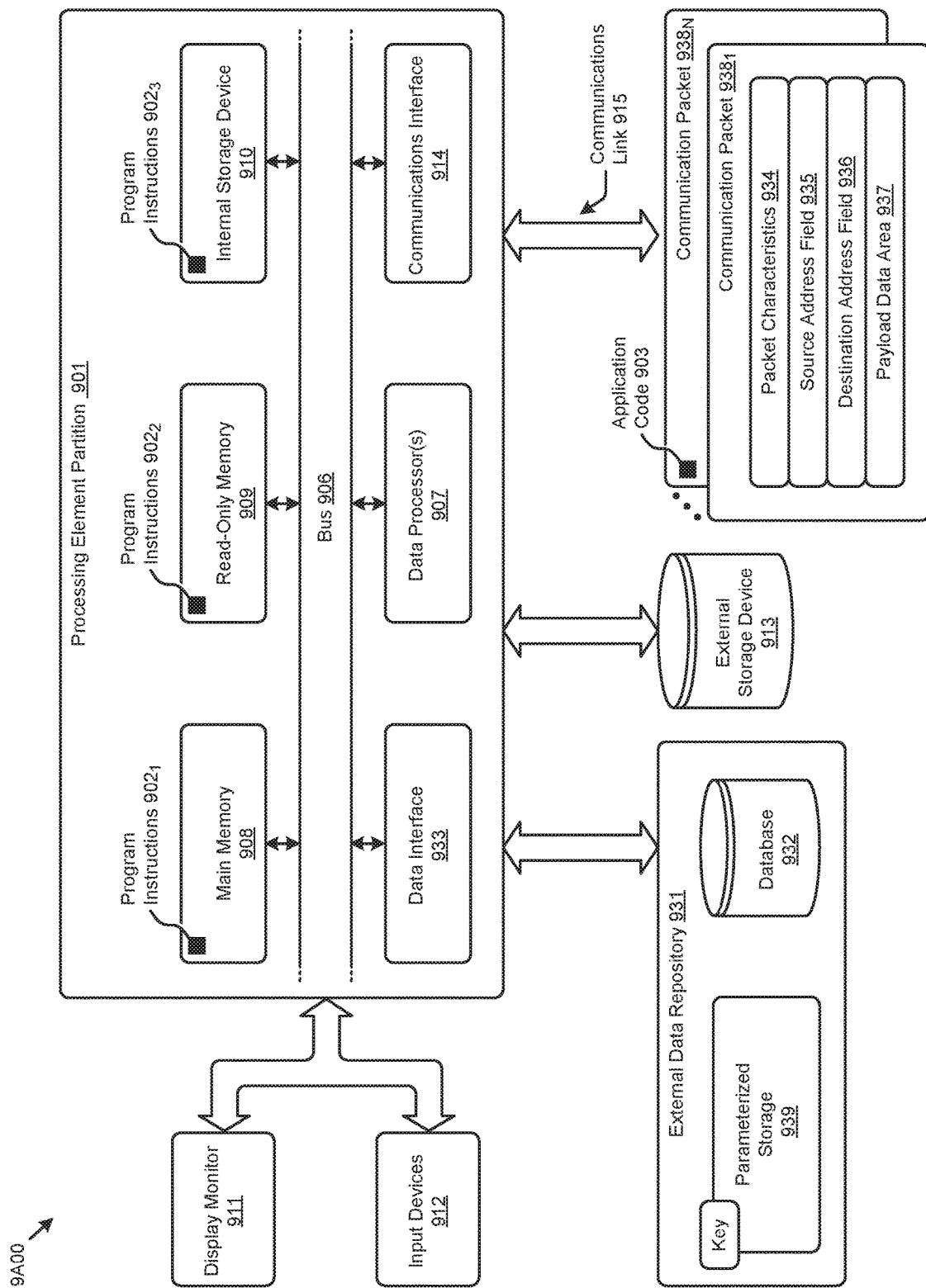
FIG. 9A and FIG. 9B present block diagrams of computer system architectures having components suitable for implementing embodiments of the present disclosure, and/or for use in the herein-described environments.

FIG. 9A depicts a block diagram of an instance of a computer system 9A00 suitable for implementing embodiments of the present disclosure. Computer system 9A00 includes a bus 906 or other communication mechanism for communicating information. The bus interconnects subsystems and devices such as a central processing unit (CPU), or a multi-core CPU (e.g., data processor 907), a system memory (e.g., main memory 908, or an area of random access memory (RAM)), a non-volatile storage device or non-volatile storage area (e.g., read-only memory 909), an internal storage device 910 or external storage device 913

(e.g., magnetic or optical), a data interface 933, a communications interface 914 (e.g., PHY, MAC, Ethernet interface, modem, etc.). The aforementioned components are shown within processing element partition 901, however other partitions are possible. Computer system 9A00 further comprises a display 911 (e.g., CRT or LCD), various input devices 912 (e.g., keyboard, cursor control), and an external data repository 931.

According to an embodiment of the disclosure, computer system 9A00 performs specific operations by data processor 907 executing one or more sequences of one or more program instructions contained in a memory. Such instructions (e.g., program instructions $902_1$, program instructions $902_2$, program instructions $902_3$, etc.) can be contained in or can be read into a storage location or memory from any computer readable/usable storage medium such as a static storage device or a disk drive. The sequences can be organized to be accessed by one or more processing entities configured to execute a single process or configured to execute multiple concurrent processes to perform work. A processing entity can be hardware-based (e.g., involving one or more cores) or software-based, and/or can be formed using a combination of hardware and software that implements logic, and/or can carry out computations and/or processing steps using one or more processes and/or one or more tasks and/or one or more threads or any combination thereof.

According to an embodiment of the disclosure, computer system 9A00 performs specific networking operations using one or more instances of communications interface 914. Instances of communications interface 914 may comprise one or more networking ports that are configurable (e.g., pertaining to speed, protocol, physical layer characteristics, media access characteristics, etc.) and any particular instance of communications interface 914 or port thereto can be configured differently from any other particular instance. Portions of a communication protocol can be carried out in whole or in part by any instance of communications interface 914, and data (e.g., packets, data structures, bit fields, etc.) can be positioned in storage locations within communications interface 914, or within system memory, and such data can be accessed (e.g., using random access addressing, or using direct memory access DMA, etc.) by devices such as data processor 907.

Communications link 915 can be configured to transmit (e.g., send, receive, signal, etc.) any types of communications packets (e.g., communication packet $938_1$, communication packet $938_N$) comprising any organization of data items. The data items can comprise a payload data area 937, a destination address 936 (e.g., a destination IP address), a source address 935 (e.g., a source IP address), and can include various encodings or formatting of bit fields to populate packet characteristics 934. In some cases, the packet characteristics include a version identifier, a packet or payload length, a traffic class, a flow label, etc. In some cases, payload data area 937 comprises a data structure that is encoded and/or formatted to fit into byte or word boundaries of the packet.

In some embodiments, hard-wired circuitry may be used in place of or in combination with software instructions to implement aspects of the disclosure. Thus, embodiments of the disclosure are not limited to any specific combination of hardware circuitry and/or software. In embodiments, the term "logic" shall mean any combination of software or hardware that is used to implement all or part of the disclosure.

The term "computer readable medium" or "computer usable medium" as used herein refers to any medium that participates in providing instructions to data processor 907 for execution. Such a medium may take many forms including, but not limited to, non-volatile media and volatile media. Non-volatile media includes, for example, optical or magnetic disks such as disk drives or tape drives. Volatile media includes dynamic memory such as RAM.

Common forms of computer readable media include, for example, floppy disk, flexible disk, hard disk, magnetic tape, or any other magnetic medium; CD-ROM or any other optical medium; punch cards, paper tape, or any other physical medium with patterns of holes; RAM, PROM, EPROM, FLASH-EPROM, or any other memory chip or cartridge, or any other non-transitory computer readable medium. Such data can be stored, for example, in any form of external data repository 931, which in turn can be formatted into any one or more storage areas, and which can comprise parameterized storage 939 accessible by a key (e.g., filename, table name, block address, offset address, etc.).

Execution of the sequences of instructions to practice certain embodiments of the disclosure are performed by a single instance of a computer system 9A00. According to certain embodiments of the disclosure, two or more instances of computer system 9A00 coupled by a communications link 915 (e.g., LAN, public switched telephone network, or wireless network) may perform the sequence of instructions required to practice embodiments of the disclosure using two or more instances of components of computer system 9A00.

Computer system 9A00 may transmit and receive messages such as data and/or instructions organized into a data structure (e.g., communications packets). The data structure can include program instructions (e.g., application code 903), communicated through communications link 915 and communications interface 914. Received program instructions may be executed by data processor 907 as it is received and/or stored in the shown storage device or in or upon any other non-volatile storage for later execution. Computer system 9A00 may communicate through a data interface 933 to a database 932 on an external data repository 931. Data items in a database can be accessed using a primary key (e.g., a relational database primary key).

Processing element partition 901 is merely one sample partition. Other partitions can include multiple data processors, and/or multiple communications interfaces, and/or multiple storage devices, etc. within a partition. For example, a partition can bound a multi-core processor (e.g., possibly including embedded or co-located memory), or a partition can bound a computing cluster having plurality of computing elements, any of which computing elements are connected directly or indirectly to a communications link. A first partition can be configured to communicate to a second partition. A particular first partition and particular second partition can be congruent (e.g., in a processing element array) or can be different (e.g., comprising disjoint sets of components).

A module as used herein can be implemented using any mix of any portions of the system memory and any extent of hard-wired circuitry including hard-wired circuitry embodied as a data processor 907. Some embodiments include one or more special-purpose hardware components (e.g., power control, logic, sensors, transducers, etc.). Some embodiments of a module include instructions that are stored in a memory for execution so as to facilitate operational and/or performance characteristics pertaining to measuring the performance of workflows performed over multiple applications. A module may include one or more state machines and/or combinational logic used to implement or facilitate the operational and/or performance characteristics pertaining to measuring the performance of workflows performed over multiple applications.

Various implementations of database 932 comprise storage media organized to hold a series of records or files such that individual records or files are accessed using a name or key (e.g., a primary key or a combination of keys and/or query clauses). Such files or records can be organized into one or more data structures (e.g., data structures used to implement or facilitate aspects of measuring the performance of workflows performed over multiple applications). Such files, records, or data structures can be brought into and/or stored in volatile or non-volatile memory. More specifically, the occurrence and organization of the foregoing files, records, and data structures improve the way that the computer stores and retrieves data in memory, for example, to improve the way data is accessed when the computer is performing operations pertaining to measuring the performance of workflows performed over multiple applications, and/or for improving the way data is manipulated when performing computerized operations pertaining to linking content object interactions that are performed across multiple applications so as to generate performance measurements of workflows that comprise the interactions.

Figure 9B:
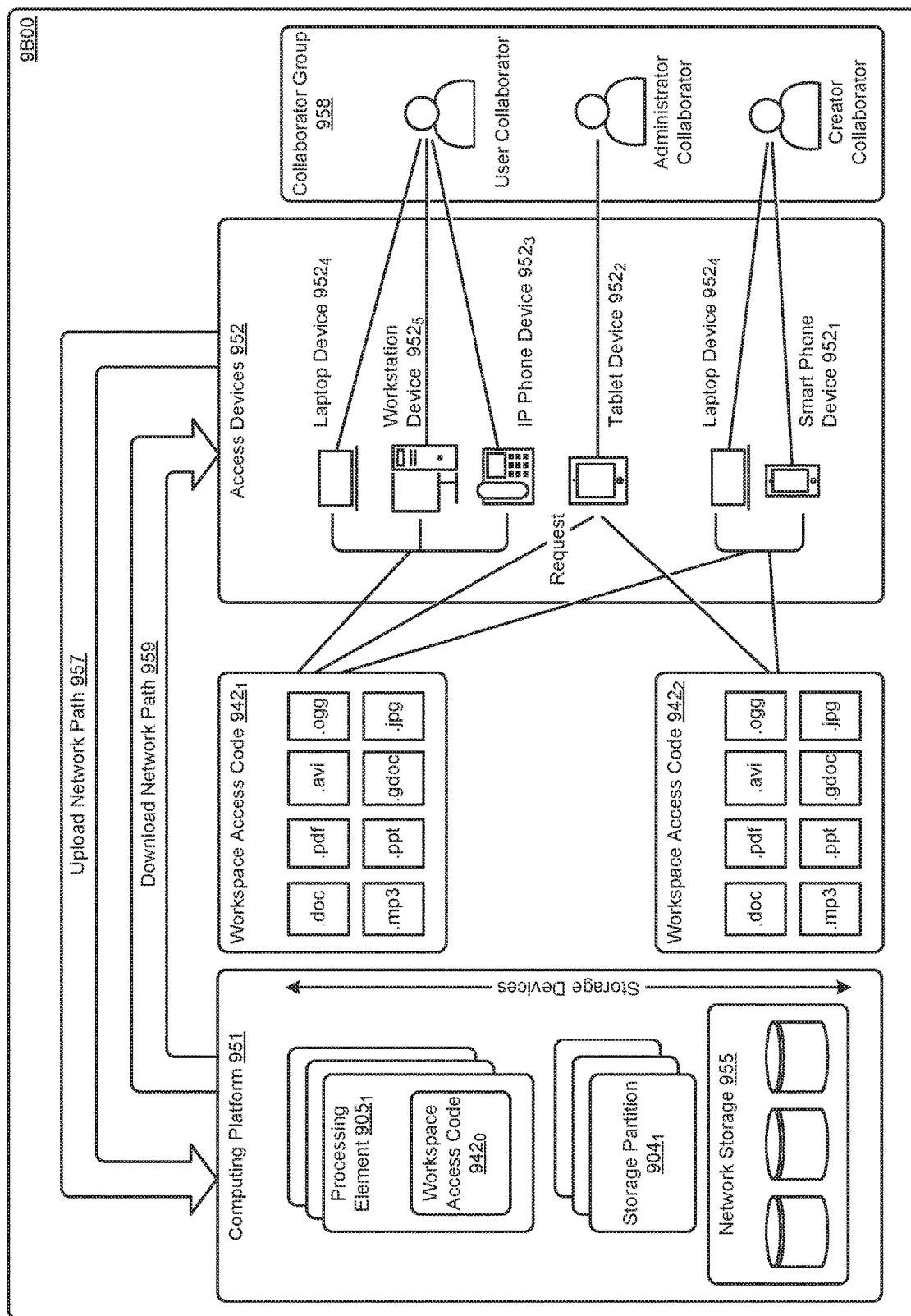

FIG. 9B depicts a block diagram of an instance of a cloud-based environment 9B00. Such a cloud-based environment supports access to workspaces through the execution of workspace access code (e.g., workspace access code $942_0$, workspace access code $942_1$, and workspace access code $942_2$). Workspace access code can be executed on any of access devices 952 (e.g., laptop device $952_4$, workstation device $952_5$, IP phone device $952_3$, tablet device $952_2$, smart phone device $952_1$, etc.), and can be configured to access any type of object. Strictly as examples, such objects can be folders or directories or can be files of any filetype. A group of users can form a collaborator group 958, and a collaborator group can be composed of any types or roles of users. For example, and as shown, a collaborator group can comprise a user collaborator, an administrator collaborator, a creator collaborator, etc. Any user can use any one or more of the access devices, and such access devices can be operated concurrently to provide multiple concurrent sessions and/or other techniques to access workspaces through the workspace access code.

A portion of workspace access code can reside in and be executed on any access device. Any portion of the workspace access code can reside in and be executed on any computing platform 951, including in a middleware setting. As shown, a portion of the workspace access code resides in and can be executed on one or more processing elements (e.g., processing element $905_1$). The workspace access code can interface with storage devices such as networked storage 955. Storage of workspaces and/or any constituent files or objects, and/or any other code or scripts or data can be stored in any one or more storage partitions (e.g., storage partition $904_1$). In some environments, a processing element includes forms of storage, such as RAM and/or ROM and/or FLASH, and/or other forms of volatile and non-volatile storage.

A stored workspace can be populated via an upload (e.g., an upload from an access device to a processing element over an upload network path 957). A stored workspace can be delivered to a particular user and/or shared with other particular users via a download (e.g., a download from a processing element to an access device over a download network path 959).

In the foregoing specification, the disclosure has been described with reference to specific embodiments thereof. It will however be evident that various modifications and changes may be made thereto without departing from the broader spirit and scope of the disclosure. For example, the above-described process flows are described with reference to a particular ordering of process actions. However, the ordering of many of the described process actions may be changed without affecting the scope or operation of the disclosure. The specification and drawings are to be regarded in an illustrative sense rather than in a restrictive sense.

What is claimed is:

1. A method for providing performance analytics, the method comprising:

establishing one or more network communication links between a content management system that manages a plurality of shared content objects and a plurality of applications that are executed by a plurality of user devices to collaborate on a shared content object of the plurality of shared content object in a workflow, one or more shared content objects of the plurality of shared content objects being modifiable by two or more applications of the plurality of applications in a respective workflow;

receiving, at a first application programming interface (API) of the content management system from a first application that is invoked by a first user device of the plurality of user devices, a first inter-process communication pertaining to a first interaction event generated by the first application in response to a first modification or creation of contents of the shared content object by the first application of the plurality of applications;

receiving, at a second API from a second application that is invoked by a second user device of the plurality of user devices, a second inter-process communication pertaining to a second interaction event generated by the second application in response to a second modification or the creation of the contents of the shared content object by the second application of the plurality of applications;

receiving, at the first API, a first API call comprising a first link attribute from the first application;

receiving, at the second API, a second API call comprising a second link attribute from the second application;

linking, at the content management system, the first interaction event and the second interaction event based at least in part upon the first link attribute and the second link attribute, wherein the first interaction event and the second interaction event both modify a same object, the same object being the shared content object modified by both the first interaction event and the second interaction event;

populating, by the content management system, data pertaining to the first and the second link attributes into a data structure that interrelates the first event interaction with the second event interaction, wherein the data structure comprises a metric attribute field that identifies the same object for which the contents are modified by both the first interaction event and the second interaction event; and generating a performance measurement of the workflow based at least in part on the data structure comprising the metric attribute field.

2. The method of claim 1, wherein linking the first interaction event and the second interaction event is processed for interaction events performed by the plurality of applications where the plurality of applications comprise different types of applications, and data normalization is performed to normalize at least one attribute type retrieved from the different types of applications.

3. The method of claim 1, wherein the first and the second interaction events performed by the plurality of applications are characterized by a plurality of event attributes, and the shared content object is a file that is modified by the first application and the second application.

4. The method of claim 3, wherein the plurality of event attributes comprises one or more link attributes that are included in the first API call or the second API call.

5. The method of claim 1, wherein the performance measurement is generated based at least in part on at least one of a workflow definition, an interaction definition, or a metric definition.

6. The method of claim 1, wherein an app registry is populated with one or more application attributes in response to the plurality of applications being registered with the content management system, and at least a portion of the app registry is locally accessible by one or more user devices that are connected to the content management system via the one or more network communication links.

7. The method of claim 1, wherein the plurality of applications comprise at least one of a native application and a third-party application, the first application comprises a document editing tool that modifies or creates the contents of the shared content object into modified contents for the first modification, and the second application comprises a different document editing tool that modifies the contents or the modified contents of the shared content object for the first modification.

8. The method of claim 1, wherein the first and the second interaction events associated with one or more of the plurality of applications comprise one or more interaction definition attributes and at least one of one or more application attributes, one or more object attributes, one or more user attributes, one or more link attributes, one or more workflow definition attributes, wherein the one or more interaction definition attributes include information of an interaction type of a plurality of interaction types, and the plurality of interaction types comprises a first interaction type for editing the contents of the shared content object and a second interaction type for authoring the contents.

9. The method of claim 1, wherein the first interaction event is raised by the first application and comprises a start event that is identified by a first interaction identifier stored in a first field of the data structure, the second interaction event is raised by the second application and comprises an end event that is identified by a second interaction identifier stored in a second field of the data structure, and the data structure further comprises a plurality of additional fields including the metric attribute field and respective storing corresponding metric identifiers of a plurality of metrics associated with the respective workflow.

10. A non-transitory computer readable medium having stored thereon a sequence of instructions which, when executed by a processor causes a set of acts for providing performance analytics, the set of acts comprising:

establishing one or more network communication links between a content management system that manages a plurality of shared content objects and a plurality of applications that are used to collaborate on a shared content object of the plurality of shared content object, one or more shared content objects of the plurality of shared content objects being modifiable by two or more applications of the plurality of applications in accordance with a respective workflow;

receiving, at a first application programming interface (API) of the content management system from a first application that is invoked by a first user device of the plurality of user devices, a first inter-process communication pertaining to a first interaction event generated by the first application in response to a first modification or creation of contents of the shared content object by the first application of the plurality of applications;

receiving, at a second API from a second application that is invoked by a second user device of the plurality of user devices, a second inter-process communication pertaining to a second interaction event generated by the second application in response to a second modification or the creation of the contents of the shared content object by the second application of the plurality of applications;

receiving, at the first API, a first API call comprising a first link attribute from the first application;

receiving, at the second API, a second API call comprising a second link attribute from the second application;

linking, at the content management system, the first interaction event and the second interaction event based at least in part upon the first link attribute and the second link attribute, wherein the first interaction event and the second interaction event both modify a same object, the same object being the shared content object modified by both the first interaction event and the second interaction event;

populating, by the content management system, data pertaining to the first and the second link attributes into a data structure that interrelates the first event interaction with the second event interaction, wherein the data structure comprises a metric attribute field that identifies the same object for which the contents are modified by both the first interaction event and the second interaction event; and generating a performance measurement of the workflow based at least in part on the data structure comprising the metric attribute field.

11. The non-transitory computer readable medium of claim 10, wherein an app registry is populated with one or more application attributes in response to the plurality of applications being registered with the content management system, and at least a portion of the app registry is locally accessible by one or more user devices that are connected to the content management system via the one or more network communication links.

12. The non-transitory computer readable medium of claim 10, wherein the act of linking is processed for interaction events performed at the plurality of applications where the plurality of applications comprise different types of applications, and data normalization is performed to normalize at least one attribute type retrieved from the different types of applications.

13. The non-transitory computer readable medium of claim 10, wherein interaction events performed at the plurality of applications are linked by a plurality of event attributes.

14. The non-transitory computer readable medium of claim 13, wherein the plurality of event attributes comprise one or more link attributes that are included in the first API call or the second API call.

15. The non-transitory computer readable medium of claim 10, wherein the performance measurement is generated based at least in part on at least one of a workflow definition, an interaction definition, or a metric definition.

16. The non-transitory computer readable medium of claim 10, wherein the plurality of applications comprise at least one of a native application and a third-party application, the first application comprises a document editing tool that modifies or creates the contents of the shared content object into modified contents for the first modification, and the second application comprises a different document editing tool that modifies the contents or the modified contents of the shared content object for the first modification.

17. The non-transitory computer readable medium of claim 10, wherein the first and the second interaction events associated with one or more of the plurality of applications comprise one or more interaction definition attributes and at least one of one or more application attributes, one or more object attributes, one or more user attributes, one or more link attributes, one or more workflow definition attributes, wherein the one or more interaction definition attributes include information of an interaction type of a plurality of interaction types, and the plurality of interaction types comprises a first interaction type for editing the contents of the shared content object and a second interaction type for authoring the contents.

18. The non-transitory computer readable medium of claim 10, wherein the first interaction event is raised by the first application and comprises a start event that is identified by a first interaction identifier stored in a first field of the data structure, the second interaction event is raised by the second application and comprises an end event that is identified by a second interaction identifier stored in a second field of the data structure, and the data structure further comprises a plurality of additional fields including the metric attribute field and respective storing corresponding metric identifiers of a plurality of metrics associated with the respective workflow.

19. A system for providing performance analytics of a project, the system comprising:
a non-transitory storage medium having stored thereon a sequence of instructions; and
one or more processors that execute the sequence of instructions, execution of the sequence of instructions causes the one or more processors to perform a set of acts, the set of acts comprising,
establishing one or more network communication links between a content management system that manages a plurality of shared content objects and a plurality of applications that are used to collaborate on a shared content object of the plurality of shared content object, one or more shared content objects of the plurality of shared content objects being modifiable by two or more applications of the plurality of applications in accordance with a respective workflow;
receiving, at a first application programming interface (API) of the content management system from a first application that is invoked by a first user device of the plurality of user devices, a first inter-process communication pertaining to a first interaction event generated by the first application in response to a first modification or creation of contents of the shared content object by the first application of the plurality of applications;
receiving, at a second API from a second application that is invoked by a second user device of the plurality of user devices, a second inter-process communication pertaining to a second interaction event generated by the second application in response to a second modification or the creation of the contents of the shared content object by the second application of the plurality of applications;
receiving, at the first API, a first API call comprising a first link attribute from the first application;
receiving, at the second API, a second API call comprising a second link attribute from the second application;
linking, at the content management system, the first interaction event and the second interaction event based at least in part upon the first link attribute and the second link attribute, wherein the first interaction event and the second interaction event both modify a same object, the same object being the shared content object modified by both the first interaction event and the second interaction event;
populating, by the content management system, data pertaining to the first and the second link attributes data into a data structure that interrelates the first event interaction with the second event interaction, wherein the data structure comprises a metric attribute field that identifies the same object for which the contents are modified by both the first interaction event and the second interaction event; and
generating a performance measurement of the workflow based at least in part on the data structure comprising the metric attribute field.

20. The system of claim 19, wherein the first interaction event is raised by the first application and comprises a start event that is identified by a first interaction identifier stored in a first field of the data structure, the second interaction event is raised by the second application and comprises an end event that is identified by a second interaction identifier stored in a second field of the data structure, and the data structure further comprises a plurality of additional fields including the metric attribute field and respective storing corresponding metric identifiers of a plurality of metrics associated with the respective workflow.

* * * * *